US007772202B2

(12) United States Patent
Dangsheng et al.

(10) Patent No.: US 7,772,202 B2
(45) Date of Patent: Aug. 10, 2010

(54) METHODS FOR TREATING BREAST CANCER USING NRIF3 RELATED MOLECULES

(75) Inventors: Li Dangsheng, Forest Hills, NY (US); Sharmistha Das, Seaucus, NJ (US); Herbert Samuels, New Rochelle, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 11/834,853

(22) Filed: Aug. 7, 2007

(65) Prior Publication Data
US 2008/0182794 A1 Jul. 31, 2008

Related U.S. Application Data

(62) Division of application No. 11/068,717, filed on Feb. 23, 2005, now abandoned.

(60) Provisional application No. 60/548,758, filed on Feb. 26, 2004.

(51) Int. Cl.
*C07H 21/04* (2006.01)
*C12N 15/00* (2006.01)
*C12N 15/12* (2006.01)

(52) U.S. Cl. .................. 514/44; 536/23.5; 435/320.1

(58) Field of Classification Search .................. None
See application file for complete search history.

(56) References Cited

U.S. PATENT DOCUMENTS 5,585,463 A * 12/1996 Shattil et al. .................. 530/350
6,639,064 B1 10/2003 Li et al.
6,783,961 B1 * 8/2004 Edwards et al. ............. 435/91.1

FOREIGN PATENT DOCUMENTS

WO           03080640        10/2003

OTHER PUBLICATIONS

Ausubel et al (Current Protocols in Molecular Biology, 1995, 3rd edition, Wiley & Sons, NY, Section9, p. 9-1 to 9-14).*
Freshney (Culture of Animal Cells, A Manual of Basic Technique, Alan R. Liss, Inc., 1983, New York, p4).*
Dermer (Bio/Technology, 1994, 12:320).*
Zips et al. (2005, In Vivo, 19:1-7).*
Li et al. The NRIF3 family of transcriptional coregulators induces rapid and profound apoptosis in breast cancer cells. Molecular and Cellular Biology. 2004, vol. 24, pp. 3838-3848.
International Search Report for International Patent Application No. PCT/US05/06237, dated Jan. 30, 2006.
Adam, Stephen A., et al., "Cytosolic Proteins That Specifically Bind Nuclear Location Signals Are Receptors for Nuclear Import", Cell, Sep. 6, 1991, vol. 66, pp. 837-847.

Afonja, Olubunmi, et al., "RAR agonists stimulate SOX9 gene expression in breast cancer cell lines: evidence for a role in retinoid-mediated growth inhibition", Oncogene, 2002, vol. 21, pp. 7850-7860.
Antonsson, Bruno, "Bax and other pro-apoptotic Bcl-2 family "killer-proteins" and their victim, the mitochondrion", Cell Tissue Res., 2001, vol. 306, pp. 347-361.
Baliga, Belinda C., et al., "Role of Prodomain in Importin-mediated Nuclear Localization and Activiation of Caspase-2", The Journal of Biological Chemistry, Feb. 14, 2003, vol. 278, No. 7, pp. 4899-4905.
Benson, John R., et al., "Update on clinical role of tamoxifen", Curr. Opin. Obstet. Gynecol., vol. 15, pp. 13-23.
Boatright, Kelly M., et al., "A Unified Model for Apical Caspase Activation", Molecular Cell, Feb. 2003, vol. 11, pp. 529-541.
Borner, Christopher, "The Bcl-2 protein family: sensors and checkpoints for life-or-death decisions", Molecular Immunology, 2003, vol. 39, pp. 615-647.
Cande, Celine, et al., "Apoptosis-inducing factor (AIF): a novel caspase-independent death effector released from mitochondria", Biochimie, 2002, vol. 84, pp. 215-222.
Chang, David W., et al., "Oligomerization Is a General Mechanism for the Activation of Apoptosis Initiator and Inflammatory Procaspases", The Journal of Biological Chemistry, May 9, 2003, vol. 278, No. 19, pp. 16466-16469.
Chen, Guoqing, et al., "TNF-R1 Signaling: A Beautiful Pathway", Science, May 31, 2002, vol. 296, pp. 1634-1635.
Cohen, Gerald M., "Caspases: the executioners of apoptosis", Biochem. J., 1997, vol. 326, pp. 1-16.
Colussi, Paul A., et al., "Prodomain-dependent Nuclear Localization of the Caspase-2 (Nedd2) Precursor", The Journal of Biological Chemistry, Sep. 18, 1998, vol. 273, No. 38, pp. 24535-24542.
Dimri, Goberdhan P., et al., "The Bmi-1 Oncogene Induces Telomerase Activity and Immortalizes Human Mammary Epithelial Cells", Cancer Research, Aug. 15, 2002, vol. 62, pp. 4736-4745.
Ekert, P. G., et al., "Caspase inhibitors", Cell Death and Differentiation, 1996, vol. 6, pp. 1081-1086.

(Continued)

*Primary Examiner*—Laura B Goddard
(74) *Attorney, Agent, or Firm*—Fish & Richardson P.C.

(57) ABSTRACT

Disclosed herein is the discovery that administration of the NRIF3 family of transcriptional coregulators (NRIF3 and related molecules) to breast cancer cells induce rapid and profound apoptosis (nearly 100% cell death within 24 h). A novel death domain (DD1) was mapped to a short 30 amino acid region common to all members of the NRIF3 family. Two other death domains (DD2 and DD3) were also found to have effective breast cancer killing activities. Mechanistic studies showed that DD1-induced apoptosis occurred through a novel caspase-2 mediated pathway that involved mitochondria membrane permeabilization but did not require other caspases. Interestingly, cytotoxicity of NRIF3 related molecules was cell-type specific, as they selectively killed breast cancer or related cells but not other examined cells of different origins, suggesting the presence in breast cancer cells of a specific death switch that can be selectively triggered by NRIF3 and related molecules. Also disclosed are strategies utilizing NRIF3 related molecules and/or targeting this death switch for the development of novel and more selective therapeutics against breast cancer.

5 Claims, 25 Drawing Sheets
(11 of 25 Drawing Sheet(s) Filed in Color)

OTHER PUBLICATIONS

Fitzgerald, Patrick, et al., "Retinoic Acid Recepetor α Expression Correlates with Retinoid-induced Growth Inhibition of Human Breast Cancer Cells Regardless of Estrogen Receptor Status", Cancer Research, Jul. 1, 1997, vol. 57, pp. 2642-2650.

Gavrieli, Yael, et al., "Identification of Programmed Cell Death in Situ via Specific Labeling of Nuclear DNA Fragmentation", J. Cell Biol., Nov. 1992, vol. 119, No. 3, pp. 493-501.

Guo, Yin, et al., "Caspase-2 Induces Apoptosis by Releasing Proapoptotic Proteins from Mitochondria", The Journal of Biological Chemistry, Apr. 19, 2002, vol. 277, No. 16, pp. 13430-13437.

Hengartner, Michael O., "The biochemistry of apoptosis", Nature, Oct. 12, 2000, vol. 407, pp. 770-776.

Homburg, Christa H. E., et al., "Human Neutrophils Lose Their Surface FcγRIII and Acquire Annexin V Binding Sites During Apoptosis in Vitro", Blood, Jan. 15, 1995, vol. 85, No. 2, pp. 532-540.

Johnstone, Ricky W., et al., "Apoptosis: A Link between Cancer Genetics and Chemotherapy", Cell, Jan. 25, 2002, vol. 108, pp. 153-164.

Kastner, Philippe, et al., "Nonsteroid Nuclear Receptors: What Are Genetic Studies Telling Us about Their Role in Real Life?", Cell, Dec. 15, 1995, vol. 83, pp. 859-869.

Kastner, Philippe, et al., "Genetic evidence that the retinoid signals is transduced by heterodimeric RXR/RAR functional units during mouse development", Development, 1997, vol. 124, pp. 313-326.

Kumar, R., et al., "Apoptosis in mammary gland and cancer", Endocrine-Related Cancer, 2000, vol. 7, pp. 257-269.

Kumar, Sharad, et al., "A Cinderella Caspase Takes Center Stage", Science, Aug. 23, 2002, vol. 297, pp. 1290-1291.

Kuwana, Tomomi, et al., "Bid, Bax, and Lipids Cooperate to Form Supramolecular Openings in the Outer Mitochondrial Membrane", Cell, Nov. 1, 2002, vol. 111, pp. 331-342.

Lahm, Armin, et al., "Death fold domain interaction in apoptosis", Cell Death and Differentiation, 2002, vol. 10, pp. 10-12.

Lassus, Patrice, et al., "Requirement for Caspase-2 in Stress-Induced Apoptosis Before Mitochondrial Permeabilization", Science, Aug. 23, 2002, vol. 297, pp. 1352-1354.

Li, Dangsheng, et al., "NRIF3 Is a Novel Coactivator Mediating Functional Specificity of Nuclear Hormone Receptors", Molecular and Cellular Biology, Oct. 1999, vol. 19, No. 10, pp. 7191-7202.

Li, Dangsheng, et al., "Domain Structure of the NRIF3 Family of Coregulators Suggests Potential Dual Roles in Transcriptional Regulation", Molecular and Cellular Biology, Dec. 2001, vol. 21, No. 24, pp. 8371-8384.

Li, Honglin, et al., "Cleavage of BID by Caspase 8 Mediates the Mitochondrial Damage in the Fas Pathway of Apoptosis", Cell, Aug. 21, 1998, vol. 94, pp. 491-501.

Loeffler, Markus, et al., "Dominant cell death induction by extramitochondrially targeted apoptosis-inducing factor", Faseb J., vol. 15, pp. 758-767.

Madesh, Muniswamy, et al., "Rapid Kinetics of tBid-induced Cytochrome c and Smac/DIABLO Release and Mitochondrial Depolarization", The Journal of Biological Chemistry, Feb. 15, 2002, vol. 277, No. 7, pp. 5651-5659.

Mangelsdorf, David J., et al., "The Nuclear Receptor Superfamily: The Second Decade", Cell, Dec. 15, 1995, vol. 83, pp. 835-839.

Miura, Masayuki, et al., "Tumor necrosis factor-induced apoptosis is mediated by a CrmA-sensitive cell death pathway", Proc. Natl. Acad. Sci. USA, Aug. 1995, vol. 92, pp. 8318-8322.

Nicholson, Donald W., "From bench to clinic with apoptosis-based therapeutic agents", Nature, Oct. 12, 2000, vol. 407, pp. 810-816.

Ohtoshi, A., et al., "Analysis of β3-endonexin mutants for their ability to interact with cyclin A", Mol. Genet. Genomics, 2001, vol. 266, pp. 664-671.

Paroni, Gabriela, et al., "Caspase-2 Can Trigger Cytochrome c Release and Apoptosis from the Nucleus", The Journal of Biological Chemistry, Apr. 26, 2002, vol. 277, No. 17, pp. 15147-15161.

Penninger, Josef M., et al., "Mitochondria, AIF and caspases—rivaling for cell death execution", Nature Cell Biology, Feb. 2003, vol. 5, pp. 97-99.

Raffo, Patrizia, et al., "Retinoid Receptors: Pathways of Proliferation Inhibition and Apoptosis Induction in Breast Cancer Cell Lines", Anticancer Research, 2000, vol. 20, pp. 1535-1544.

Read, Stuart H., et al., "A novel Apaf-1-independent putative caspase-2 activation complex", J. Cell Biol., Dec. 9, 2002, vol. 159, No. 5, pp. 739-745.

Riggs, B. Lawrence, et al., "Selective Estrogen-Receptors Modulators—Mechanisms of Action and Application to Clinical Practice", N. Engl. J. Med., Feb. 13, 2003, vol. 348, pp. 618-629.

Robertson, John D., et al., "Caspase-2 Acts Upstream of Mitochondria to Promote Cytochrome c Release during Etoposide-induced Apoptosis", The Journal of Biological Chemistry, Aug. 16, 2002, vol. 277, No. 33, pp. 29803-29809.

Schneider, Sonja M., et al., "Activation of Retinoic Acid Receptor α Is Sufficient for Full Induction of Retinoid Responses in SK-BR-3 and T47D Human Breast Cancer Cells", Cancer Research, Oct. 1, 2000, vol. 60, pp. 5479-5487.

Shattil, Sanford J., et al., "β3-Endonexin, a Novel Polypeptide That Interacts Specifically with the Cytoplasmic Tail of the Integrin β3 Subunit", J. Cell Biol., Nov. 1995, vol. 131, No. 3, pp. 807-816.

Shikama, Yoshiaki, et al., "Comprehensive Studies on Subcellular Localizations and Cell Death-Inducing Activities of Eight GFP-Tagged Apoptosis-Related Caspases", Experimental Cell Research, 2001, vol. 264, pp. 315-325.

Susin, Santos A., et al., "Molecular characterization of mitochondrial apoptosis-inducing factor", Nature, Feb. 4, 1999, vol. 397, pp. 441-446.

Talanian, Robert V., et al., "Substrate Specificities of Caspase Family Proteases", The Journal of Biological Chemistry, Apr. 11, 1997, vol. 272, No. 15, pp. 9677-9682.

Troy, C. M., et al., "Caspase-2 redux", Cell Death and Differentiation, 2003, vol. 10, pp. 101-107.

Verhoven, Bret, et al., "Mechanisms of Phosphatidylserine Exposure, A Phagocyte Recognition Signal, on Apoptotic T Lymphocytes", J. Exp. Med., Nov. 1995, vol. 182, pp. 1597-1601.

Wang, Xiaodong, "The expanding role of mitochondria in apoptosis", Genes & Development, 2001, vol. 15, pp. 2922-2933.

Ye, Hong, et al., "DNA binding is required for the apoptogenic action of apoptosis inducing factor", Nature Structural Biology, Sep. 2002, vol. 9, No. 9, pp. 680-684.

Yoshida, Hiroshi, "The Role of Apaf-1 in Programmed Cell Death: From Worm to Tumor", Cell Structure and Function, 2003, vol. 28, pp. 3-9.

Zapata, Juan M., et al., "Expression of multiple apoptosis-regulatory genes in human breast cancer cell lines and primary tumors", Breast Cancer Research and Treatment, 1998, vol. 47, pp. 129-140.

"Adjuvant Therapy for Breast Cancer", NIH Consensus Statement, Nov. 2000, vol. 17, No. 4.

Fischer, U et al. "Apoptosis-Based Therapies and Drug Targets." Cell Death and Differentiation (2005) 12, 942-961.

Freshney, R. Ian. "Culture of Animal Cells: A Manual of Basic Technique." Alan R. Liss, Inc., 1983, New York: pp. 4.

Dermer, Gerald B. "Another Anniversary for the War on Cancer." Bio/Technology, Mar. 1994, vol. 12: 320.

Zips, Daniel et al. "New Anticancer Agents: In Vitro and In Vivo Evaluation." in vivo 19: 1-8 (2005).

Shattil, S. et al. "b3-Endonexin, a Novel Polypeptide that Interacts Specifically with the Cytoplasmic Tail of the Integrin b3 Subunit." The Journal of Cell Biology, vol. 131, No. 3, Nov. 1995, pp. 807-816.

Bowie, et al. "Deciphering the Message in Protein Sequences: Tolerance to Amino Acid Substitutions." Science, vol. 247, No1 4948, Mar. 16, 1990, pp. 1306-1310.

Wells, "Additivity of Mutational Effects in Proteins." Biochemistry, vol. 29, No. 37, Sep. 18, 1990, pp. 8509-8517.

Ngo, et al. "Computational Complexity, Protein Structure Prediction, and the Levinthal Paradox." The Protein Folding Protblem and Teritary Structure Predidtion, Merz et al., eds., 1994, pp. 433-506.

* cited by examiner

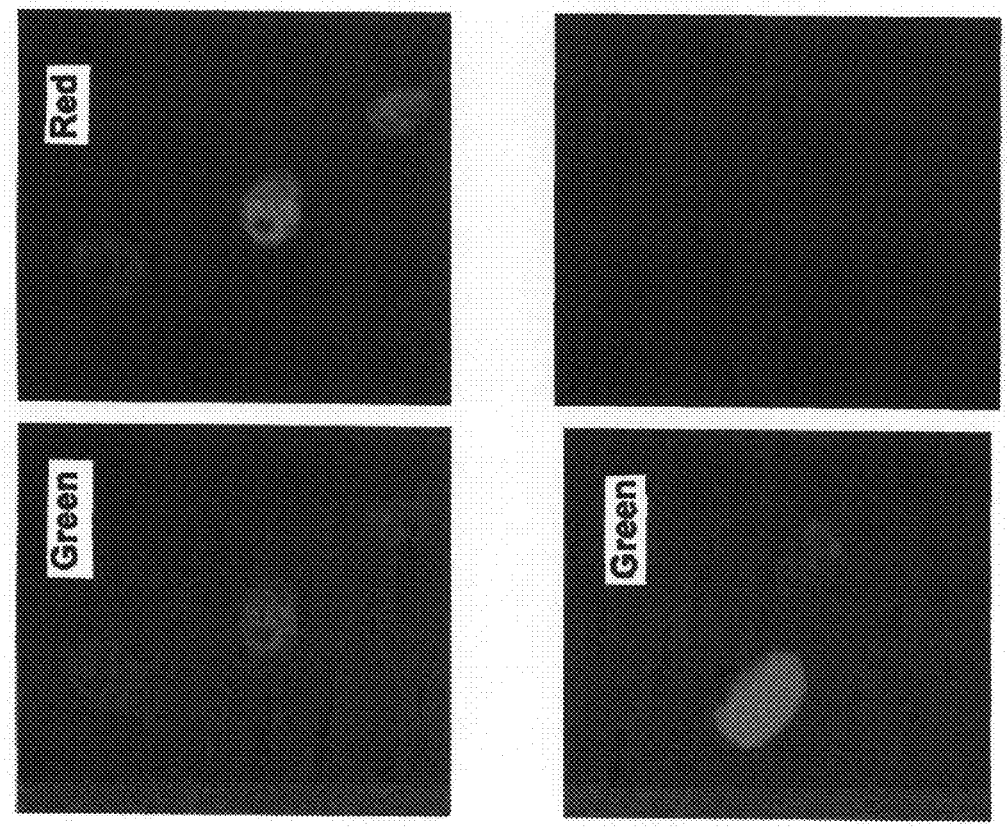

|  | Cell lines | Comments | Apoptosis Induction | |
|---|---|---|---|---|
|  |  |  | NRIF3 | DD1 |
| Breast Cancer Cells | T-47D | Human, ER+, ductal carcinoma | +++ | +++ |
|  | MCF-7 | Human, ER+, adenocarcinoma | +++ | +++ |
|  | MDA-231 | Human, ER-, adenocarcinoma | +++ | +++ |
|  | MDA-231/ER+ | MDA-231 stably expressing ER | +++ | +++ |
|  | MDA-435 | Human, ER-, ductal carcinoma | +++ | +++ |
| Non-Breast-Cancer Cells | HeLa | Human cervix adenocarcinoma | - | - |
|  | 293 | Human kidney transformed | - | - |
|  | UOK-145 | Human kidney carcinoma | - | - |
|  | Cos-1 | Monkey kidney transformed | - | - |
|  | GH4C1 | Rat pituitary tumor | - | - |

Figure 7B

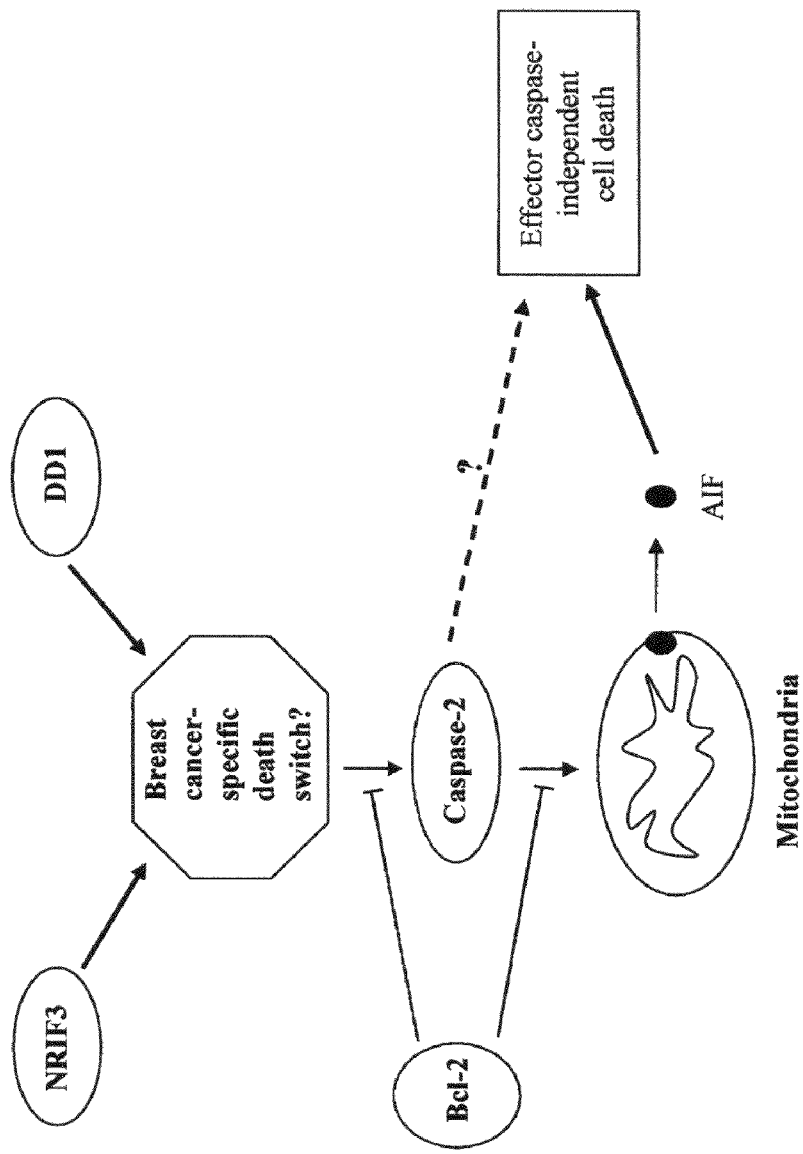

Coding sequence for full-length NRIF3

```
atgcctgtt aaaagatcac tgaagttgga tggtctgtta gaagaaaatt
catttgatcc ttcaaaaatc acaaggaaga aaagtgttat aacttattct
ccaacaactg gaacttgtca aatgagtcta tttgcttctc ccacaagttc
tgaagagcaa aagcacagaa atggactatc aaatgaaaag agaaaaaaat
tgaatcaccc cagtttaact gaaagcaaag aatctacaac aaaagacaat
gatgaattca tgatgttgct atcaaaagtt gagaaattgt cagaagaaat
catggagata atgcaaaatt taagtagtat acaggctttg gagggcagta
gagagcttga aaatctcatt ggaatctcct gtgcatcaca tttcttaaaa
agagaaatgc agaaaaccaa agaactaatg acaaaagtga ataaacaaaa
actgtttgaa aagagtacag gacttcctca caaagcatca cgtcatcttg
acagctatga attccttaaa gccattttaa ac
```

Figure 11A

Coding sequence for full-length EnS

```
atgcctgtta aaagatcact gaagttggat ggtctgttag aagaaaattc
atttgatcct tcaaaaatca caaggaagaa aagtgttata acttattctc
caacaactgg aacttgtcaa atgagtctat ttgcttctcc cacaagttct
gaagagcaaa agcacagaaa tggactatca aatgaaaaga gaaaaaatt
gaatcacccc agtttaactg aaagcaaaga atctacaaca aaagacaatg
atgaattcat gatgttgcta tcaaaagttg agaaattgtc agaagaaatc
atggagataa tgcaaaattt aagtagtata cag
```

Figure 11B

Coding sequence for full-length EnL

```
atgcctgtta aaagatcact gaagttggat ggtctgttag aagaaaattc
atttgatcct tcaaaaatca caaggaagaa aagtgttata acttattctc
caacaactgg aacttgtcaa atgagtctat ttgcttctcc cacaagttct
gaagagcaaa agcacagaaa tggactatca aatgaaaaga gaaaaaatt
gaatcacccc agtttaactg aaagcaaaga atctacaaca aaagacaatg
atgaattcat gatgttgcta tcaaaagttg agaaattgtc agaagaaatc
atggagataa tgcaaaattt aagtagtata caggctttgg agggcagtag
agagcttgaa aatctcattg aatctcctg tgcatcacat ttcttaaaaa
gagaaatgca gaaaccaaa gaactaatga caaaagtgaa taaacaaaaa
ctgtttgaaa agagtacagg acttcctcac aaaggtcagc ctcagatgtc
acaacctctg
```

Figure 11C

Coding sequence for death domain 1 (DD1)

ccttcaaaaatcacaaggaagaaaagtgttataacttattctccaacaactggaa
cttgtcaaatgagtctatttgcttctccacaagttct

Figure 12A

Coding sequence for death domain 2 (DD2)

cccacaagttctgaagagcaaaagcacagaaatggactatcaaatgaaaagagaa
aaaattgaatcacccagtttaactgaaagcaaagaatctacaacaaaagacaa
tgatgaattc

Figure 12B

Coding sequence for death domain 3 (DD3)

gctttggagggcagtagagagcttgaaaatctcattggaatctcct
gtgcatcacatttcttaaaaagagaaatgcagaaaaccaaagaactaatg
acaaaagtgaataaacaaaaactgtttgaaagagtacaggacttcctca
caaagcatcacgtcatcttgacagctatgaattccttaaagccattttaaac

Figure 12C

```
  1  CAGCGGGCAGTGGTGCTTTCCCGAATCTCAGAATGCCTGTTAAAGATCACTGAAGTTGGA
                              M  P  V  K  R  S  L  K  L  D

61  TGGTCTGTTAGAAGAAAATTCATTTGATCCTTCAAAATCACAAGGAAGAAAAGTGTTAT
      G  L  L  E  E  N  S  F  D  P  S  K  I  T  R  K  K  S  V  I

121  AACTTATTCTCCAACAACTGGAACTTGTCAAATGAGTCTATTGCTTCTCCCACAAGTTC
      T  Y  S  P  T  T  G  T  C  Q  M  S  L  F  A  S  P  T  S  S

181  TGAAGAGCAAAAGCACAGAAATGGACTATCAAATGAAAGAGAAAAAATTGAATCACCC
      E  E  Q  K  H  R  N  G  L  S  N  E  K  R  K  K  L  N  H  P

241  CAGTTTAACTGAAAGCAAAGAATCTACAACAAAGACAATGATGAATTCATGATGTTGCT
      S  L  T  E  S  K  E  S  T  T  K  D  N  D  E  F  M  M  L  L

301  ATCAAAAGTTGAGAAATGTCAGAAGAATCATGGAGATAATGCAAAATTTAAGTAGTAT
      S  K  V  E  K  L  S  E  E  I  M  E  I  M  Q  N  L  S  S  I

361  ACAGGCTTTGGAGGGCAGTAGAGAGCTTGAAAATCTCATTGGAATCTCCTGTGCATCACA
      Q  A  L  E  G  S  R  E  L  E  N  L  I  G  I  S  C  A  S  H

421  TTTCTTAAAAGAGAAATGCAAAGACCAAAGAACTAATGACAAAGTGAATAAACAAAA
      F  L  K  R  E  M  Q  K  T  K  E  L  M  T  K  V  N  K  Q  K

481  ACTGTTTGAAAAGAGTACAGGACTTCCTCACAAAGCATCAGTCATCTTGACAGCTATGA
      L  F  E  K  S  T  G  L  P  H  K  A  S  R  H  L  D  S  Y  E

541  ATTCCTTAAAGCCATTTTAAACTGAGGCATTAAGAAGAAATGCACTCACCATGAGCACCA
      F  L  K  A  I  L  N  *
```

Figure 13

SEQUENCE LISTING

<160> NUMBER OF SEQ ID NOS: 14

<210> SEQ ID NO 1
<211> LENGTH: 531
<212> TYPE: DNA
<213> ORGANISM: artificial
<220> FEATURE:
<223> OTHER INFORMATION: full-length NRIF3

<400> SEQUENCE: 1

```
atgcctgtta aaagatcact gaagttggat ggtctgttag aagaaaattc atttgatcct      60
tcaaaaatca caaggaagaa aagtgttata acttattctc caacaactgg aacttgtcaa     120
atgagtctat ttgcttctcc cacaagttct gaagagcaaa agcacagaaa tggactatca     180
aatgaaaaga gaaaaaaatt gaatcacccc agtttaactg aaagcaaaga atctacaaca     240
aaagacaatg atgaattcat gatgttgcta tcaaaagttg agaaattgtc agaagaaatc     300
atggagataa tgcaaaattt aagtagtata caggctttgg agggcagtag agagcttgaa     360
aatctcattg gaatctcctg tgcatcacat ttcttaaaaa gagaaatgca gaaaaccaaa     420
gaactaatga caaaagtgaa taaacaaaaa ctgtttgaaa agagtacagg acttcctcac     480
aaagcatcac gtcatcttga cagctatgaa ttccttaaag ccattttaaa c              531
```

<210> SEQ ID NO 2
<211> LENGTH: 333
<212> TYPE: DNA
<213> ORGANISM: artificial
<220> FEATURE:
<223> OTHER INFORMATION: full-length EnL

<400> SEQUENCE: 2

```
atgcctgtta aaagatcact gaagttggat ggtctgttag aagaaaattc atttgatcct      60
tcaaaaatca caaggaagaa aagtgttata acttattctc caacaactgg aacttgtcaa     120
atgagtctat ttgcttctcc cacaagttct gaagagcaaa agcacagaaa tggactatca     180
aatgaaaaga gaaaaaaatt gaatcacccc agtttaactg aaagcaaaga atctacaaca     240
aaagacaatg atgaattcat gatgttgcta tcaaaagttg agaaattgtc agaagaaatc     300
atggagataa tgcaaaattt aagtagtata cag                                  333
```

<210> SEQ ID NO 3
<211> LENGTH: 510
<212> TYPE: DNA
<213> ORGANISM: artificial
<220> FEATURE:
<223> OTHER INFORMATION: full-length EnS

<400> SEQUENCE: 3

```
atgcctgtta aaagatcact gaagttggat ggtctgttag aagaaaattc atttgatcct      60
tcaaaaatca caaggaagaa aagtgttata acttattctc caacaactgg aacttgtcaa     120
atgagtctat ttgcttctcc cacaagttct gaagagcaaa agcacagaaa tggactatca     180
aatgaaaaga gaaaaaaatt gaatcacccc agtttaactg aaagcaaaga atctacaaca     240
aaagacaatg atgaattcat gatgttgcta tcaaaagttg agaaattgtc agaagaaatc     300
atggagataa tgcaaaattt aagtagtata caggctttgg agggcagtag agagcttgaa     360
aatctcattg gaatctcctg tgcatcacat ttcttaaaaa gagaaatgca gaaaaccaaa     420
gaactaatga caaaagtgaa taaacaaaaa ctgtttgaaa agagtacagg acttcctcac     480
```

```
aaaggtcagc ctcagatgtc acaacctctg                                    510

<210> SEQ ID NO 4
<211> LENGTH: 93
<212> TYPE: DNA
<213> ORGANISM: artificial
<220> FEATURE:
<223> OTHER INFORMATION: sequence of DD1

<400> SEQUENCE: 4
ccttcaaaaa tcacaaggaa gaaaagtgtt ataacttatt ctccaacaac tggaacttgt    60
caaatgagtc tatttgcttc tcccacaagt tct                                93

<210> SEQ ID NO 5
<211> LENGTH: 120
<212> TYPE: DNA
<213> ORGANISM: artificial
<220> FEATURE:
<223> OTHER INFORMATION: sequence of DD2

<400> SEQUENCE: 5
cccacaagtt ctgaagagca aaagcacaga atggactat caaatgaaaa gagaaaaaaa    60
ttgaatcacc ccagtttaac tgaaagcaaa gaatctacaa caaaagacaa tgatgaattc   120

<210> SEQ ID NO 6
<211> LENGTH: 198
<212> TYPE: DNA
<213> ORGANISM: artificial
<220> FEATURE:
<223> OTHER INFORMATION: sequence of DD3

<400> SEQUENCE: 6
gctttggagg gcagtagaga gcttgaaaat ctcattggaa tctcctgtgc atcacatttc    60
ttaaaaagag aaatgcagaa aaccaaagaa ctaatgacaa aagtgaataa acaaaaactg   120
tttgaaaaga gtacaggact tcctcacaaa gcatcacgtc atcttgacag ctatgaattc   180
cttaaagcca ttttaaac                                                 198

<210> SEQ ID NO 7
<211> LENGTH: 600
<212> TYPE: DNA
<213> ORGANISM: artificial
<220> FEATURE:
<223> OTHER INFORMATION: NRIF3 sequence

<400> SEQUENCE: 7
cagcggcagt ggtgctttcc cgaatctcag aatgcctgtt aaaagatcac tgaagttgga    60
tggtctgtta gaagaaaatt catttgatcc ttcaaaaatc acaaggaaga aaagtgttat   120
aacttattct ccaacaactg gaacttgtca aatgagtcta tttgcttctc ccacaagttc   180
tgaagagcaa aagcacagaa atggactatc aaatgaaaag agaaaaaaat gaatcaccc   240 cagtttaact gaaagcaaag aatctacaac aaaagacaat gatgaattca tgatgttgct   300
atcaaaagtt gagaaattgt cagaagaaat catggagata atgcaaaatt taagtagtat   360
acaggctttg gagggcagta gagagcttga aatctcatt ggaatctcct gtgcatcaca   420
tttcttaaaa agagaaatgc agaaaaccaa agaactaatg acaaaagtga ataaacaaaa   480
actgtttgaa aagagtacag gacttcctca caaagcatca cgtcatcttg acagctatga   540
attccttaaa gccatttaa actgaggcat taagaagaaa tgcactcacc atgagcacca   600
```

<210> SEQ ID NO 8
<211> LENGTH: 177
<212> TYPE: PRT
<213> ORGANISM: artificial
<220> FEATURE:
<223> OTHER INFORMATION: NRIF3 sequence

<400> SEQUENCE: 8

Met Pro Val Lys Arg Ser Leu Lys Leu Asp Gly Leu Leu Glu Glu Asn
1               5                   10                  15

Ser Phe Asp Pro Ser Lys Ile Thr Arg Lys Lys Ser Val Ile Thr Tyr
            20                  25                  30

Ser Pro Thr Thr Gly Thr Cys Gln Met Ser Leu Phe Ala Ser Pro Thr
        35                  40                  45

Ser Ser Glu Glu Gln Lys His Arg Asn Gly Leu Ser Asn Glu Lys Arg
    50                  55                  60

Lys Lys Leu Asn His Pro Ser Leu Thr Glu Ser Lys Glu Ser Thr Thr
65                  70                  75                  80

Lys Asp Asn Asp Glu Phe Met Met Leu Leu Ser Lys Val Glu Lys Leu
                85                  90                  95

Ser Glu Glu Ile Met Glu Ile Met Gln Asn Leu Ser Ser Ile Gln Ala
            100                 105                 110

Leu Glu Gly Ser Arg Glu Leu Glu Asn Leu Ile Gly Ile Ser Cys Ala
        115                 120                 125

Ser His Phe Leu Lys Arg Glu Met Gln Lys Thr Lys Glu Leu Met Thr
    130                 135                 140

Lys Val Asn Lys Gln Lys Leu Phe Glu Lys Ser Thr Gly Leu Pro His
145                 150                 155                 160

Lys Ala Ser Arg His Leu Asp Ser Tyr Glu Phe Leu Lys Ala Ile Leu
                165                 170                 175

Asn

<210> SEQ ID NO 9
<211> LENGTH: 16
<212> TYPE: PRT
<213> ORGANISM: artificial
<220> FEATURE:
<223> OTHER INFORMATION: Hydrophobic sequence derived from Kaposi
      fibroblast growth factor signal sequence

<400> SEQUENCE: 9

Ala Ala Val Ala Leu Leu Pro Ala Val Leu Leu Ala Leu Leu Ala Pro
1               5                   10                  15

<210> SEQ ID NO 10
<211> LENGTH: 15
<212> TYPE: PRT
<213> ORGANISM: artificial
<220> FEATURE:
<223> OTHER INFORMATION: Cell-permeation sequence derived from the HIV
      TAT protein

<400> SEQUENCE: 10

Gly Gly Gly Tyr Gly Arg Lys Lys Arg Arg Gln Arg Arg Arg Gly
1               5                   10                  15

<210> SEQ ID NO 11
<211> LENGTH: 31
<212> TYPE: PRT
<213> ORGANISM: artificial
<220> FEATURE:

<223> OTHER INFORMATION: sequence of DD1

<400> SEQUENCE: 11

Pro Ser Lys Ile Thr Arg Lys Lys Ser Val Ile Thr Tyr Ser Pro Thr
1               5                   10                  15

Thr Gly Thr Cys Gln Met Ser Leu Phe Ala Ser Pro Thr Ser Ser
            20                  25                  30

<210> SEQ ID NO 12
<211> LENGTH: 40
<212> TYPE: PRT
<213> ORGANISM: artificial
<220> FEATURE:
<223> OTHER INFORMATION: sequence of DD2

<400> SEQUENCE: 12

Pro Thr Ser Ser Glu Glu Gln Lys His Arg Asn Gly Leu Ser Asn Glu
1               5                   10                  15

Lys Arg Lys Lys Leu Asn His Pro Ser Leu Thr Glu Ser Lys Glu Ser
                20                  25                  30

Thr Thr Lys Asp Asn Asp Glu Phe
            35                  40

<210> SEQ ID NO 13
<211> LENGTH: 66
<212> TYPE: PRT
<213> ORGANISM: artificial
<220> FEATURE:
<223> OTHER INFORMATION: sequence of DD3

<400> SEQUENCE: 13

Ala Leu Glu Gly Ser Arg Glu Leu Glu Asn Leu Ile Gly Ile Ser Cys
1               5                   10                  15

Ala Ser His Phe Leu Lys Arg Glu Met Gln Lys Thr Lys Glu Leu Met
                20                  25                  30

Thr Lys Val Asn Lys Gln Lys Leu Phe Glu Lys Ser Thr Gly Leu Pro
            35                  40                  45

His Lys Ala Ser Arg His Leu Asp Ser Tyr Glu Phe Leu Lys Ala Ile
        50                  55                  60

Leu Asn
65

<210> SEQ ID NO 14
<211> LENGTH: 59
<212> TYPE: PRT
<213> ORGANISM: artificial
<220> FEATURE:
<223> OTHER INFORMATION: beta3-endonexin long form sequence

<400> SEQUENCE: 14

Ala Leu Glu Gly Ser Arg Glu Leu Glu Asn Leu Ile Gly Ile Ser Cys
1               5                   10                  15

Ala Ser His Phe Leu Lys Arg Glu Met Gln Lys Thr Lys Glu Leu Met
                20                  25                  30

Thr Lys Val Asn Lys Gln Lys Leu Phe Glu Lys Ser Thr Gly Leu Pro
            35                  40                  45

His Lys Gly Gln Pro Gln Met Ser Gln Pro Leu
        50                  55

METHODS FOR TREATING BREAST CANCER USING NRIF3 RELATED MOLECULES

CROSS REFERENCE TO RELATED APPLICATION

This application is a Divisional of U.S. patent application Ser. No. 11/068,717, filed Feb. 23, 2005, which claims priority under 35 U.S.C. §119(e) to U.S. Provisional Application Ser. No. 60/548,758 filed Feb. 26, 2004 which is incorporated by reference herein in its entirety.

The United States Government has certain rights to this invention by virtue of funding received from grant DK 16636 from the National Institute of Health.

FIELD OF THE INVENTION

The present invention is broadly directed to the treatment of breast cancer and more specifically to the use of NRIF3 related molecules in methods for treating breast cancer in mammals and pharmaceutical formulations for use in the methods.

BACKGROUND OF THE INVENTION

Many anticancer drugs act by inducing apoptosis (20). The rapid progress in understanding mechanisms underlying apoptosis may present opportunities to harness the cellular death machinery for the benefit of treating human diseases such as cancer (20, 35). Ideally, therapeutic strategies targeting an apoptotic pathway(s) should selectively kill cancer but not other cells. At present, however, this remains a very challenging objective.

Breast cancer is the second leading cause of cancer-related deaths in women (23). Each year more than 180,000 women in the United States are diagnosed with breast cancer. Currently, effective drug treatment for breast cancer is somewhat limited. Since many early stage breast tumors express the estrogen receptor (ER), and depend on estrogen for their optimal growth, anti-estrogens (ER antagonists) have been widely used in the treatment of ER+ tumors (5, 41). Anti-estrogens, however, are not effective in ER– tumors. Also, tumors that are initially ER+ may lose ER expression and become independent of estrogen for their growth and refractory to anti-estrogen therapy.

Currently, the primary treatment of localized breast cancer is either breast-conserving surgery and radiation or mastectomy with or without breast reconstruction. Systemic adjuvant therapies are also employed to eradiate microscopic deposits of cancer cells that may have spread or metastisized from the primary tumor. Systemic adjuvant therapies include chemotherapy and hormonal therapy. Radiation is also used as a local adjuvant treatment to eradicate cancer cells in the chest wall or regional lymph nodes after mastectomy (reviewed in 54). Major acute and long-term side effects of adjuvant treatments include premature menopause, weight gain, mild memory loss and fatigue.

Apoptosis or programmed cell death is a fundamental cellular process where the affected cell dies by actively executing a coordinately regulated death program (11, 18). For multicellular organisms (e.g. mammals) apoptosis plays important roles in normal development, tissue homeostasis, and in diverse pathological processes. Caspases and mitochondria are two key cellular components involved in the execution and regulation of apoptosis (18, 50). Caspases are a group of cysteine-proteases that are ordinarily inactive in cells as pro-enzymes but are activated upon appropriate apoptotic stimuli. Generally, the initiator caspases (e.g. 2, 8, 9, and 10) are activated when complexed with adaptor molecules, resulting in either autoprocessing due to induced proximity or holoenzyme formation (9, 18, 26, 40). The downstream effector caspases (e.g. 3, 6, and 7) are activated through proteolytic cleavage by initiator caspase(s). Effector caspases then cleave various cellular components, leading to the morphologic and biochemical phenotypes characteristic of apoptosis (11, 18).

Mitochondria also play an important role in apoptosis, as various apoptotic stimuli converge on mitochondria and lead to mitochondrial membrane permeabilization (MMP) (25, 38, 50). Upon MMP, mitochondria release a number of factors that are involved in apoptosis initiation and/or execution, such as cytochrome-c, Smac/Diablo, and AIF (Apoptosis Inducing Factor) (8, 18, 38, 50). The released cytochrome-c interacts with the adaptor protein Apaf-1 and pro-caspase-9 to form an activated complex referred to as an apoptosome, which then cleaves and activates downstream effector caspases (e.g. caspase-3) (18, 52). In contrast, AIF released from mitochondria triggers apoptosis (e.g. by inducing chromatin condensation and large-scale DNA fragmentation) independent of effector caspases (8, 31, 46, 51). This caspase-independent apoptogenic function of AIF is evolutionarily conserved, and plays an important role both in normal development and in cell death processes whereby caspases are minimally activated or inhibited (e.g. by chemical inhibitors) (8, 38).

There are two major apoptotic pathways in mammalian cells (11, 18). The extrinsic pathway is initiated by the binding of transmembrane death receptors (e.g. Fas, TNF-R1, and TRAIL receptors) with cognate extracellular ligands. Liganded receptors recruit adaptor proteins (e.g. FADD) which interact with and trigger the activation of caspase-8. Activated caspase-8 then cleaves and activates downstream effector caspases such as caspase-3. In contrast, the intrinsic pathway is characterized by disruption of mitochondria membrane integrity when cells are exposed to various stresses (e.g. DNA damaging agents). Mitochondrial membrane permeabilization (MMP) triggers apoptosis via both caspase-dependent (e.g. the cytochrome-c/caspase-9 pathway) and caspase-independent (e.g. the AIF pathway) mechanisms. Crosstalk exists between the extrinsic and intrinsic pathways, as activated caspase-8 can cleave Bid to produce truncated Bid (tBid), which then binds to mitochondria and promotes MMP (30, 32). The subsequent release of cytochrome-c from mitochondria further facilitates the apoptotic process.

MMP is regulated by the Bcl-2 family of proteins, which act upstream of mitochondria, and contain both anti-apoptotic (e.g. Bcl-2 and Bcl-xL) and pro-apoptotic members (e.g. Bak, Bax, Bid, and Bad) (3, 7). The relative balance between the pro- and anti-apoptotic members of the Bcl-2 family is critical in controlling MMP. Interestingly, a number of recent studies have shown that caspase-2 acts upstream of mitochondria and is required for MMP during stress-induced apoptosis in certain cell types (17, 27, 42). While these studies implicate caspase-2 as an initiator caspase in certain intrinsic pathway(s) of apoptosis, the mechanistic interplay between caspase-2 and members of the Bcl-2 family in controlling MMP is not yet clear (24).

The present inventors have studied the role of nuclear receptors in breast cancer cell proliferation (2). U.S. Pat. No. 6,639,064, issued Oct. 28, 2003 discloses the cloning of a novel coregulator (designated as NRIF3) which specifically interacts with and enhances the activity of ligand-bound thyroid hormone receptors (TRs) and retinoid X receptors (RXRs) (28, 29). However, no therapeutic role was ascribed to the protein in these publications.

SUMMARY OF THE INVENTION

It has now been unexpectedly discovered that expression of NIRF3 and related molecules inhibits growth of breast cancer cells independent of retinoid treatment. Further studies indicate that this apparent growth inhibition resulted from the induction of rapid and profound apoptosis in these cells by NRIF3 (virtually 100% cell death within 24 h). The apoptogenic function of NRIF3 was independent of its interaction with nuclear receptors, and was mapped to a novel death domain (DD1) that is relatively small in size (~30 amino acids). Mechanistic studies suggest that DD1-induced apoptosis occurs through a novel caspase-2 mediated pathway that involves MMP and AIF translocation but does not appear to require other caspases. Cytotoxicity of NRIF3 and DD1 was cell-type specific, as their expression led to efficient apoptosis in all the breast cancer cell lines surveyed (ER+ T-47D, MCF-7, MDA-MB-231-ER+ cells and ER– MDA-MB-231 and MDA-MB-435 cells), but not in five other cell types of different origins (HeLa, GH4C1, 293, UOK145, and Cos-1).

One aspect of the present invention provides a method for treating a patient suffering from breast cancer comprising administering to a patient in need of such treatment an amount effective to treat breast cancer of an agent selected from NRIF3 related molecules and derivatives thereof.

In another aspect, the present invention provides a pharmaceutical formulation for treating a mammal suffering from breast cancer comprising NRIF3 related molecules, derivatives thereof and a pharmaceutical acceptable carrier or diluent.

In yet another aspect, the present invention provides an isolated polypeptide comprising an amino acid sequence consisting of DD1.

In still another aspect, the present invention provides an isolated polypeptide comprising an amino acid sequence consisting of DD2.

In still a further aspect of the present invention provides an isolated polypeptide comprising an amino acid sequence consisting of DD3.

In still another aspect, the present invention provides an isolated nucleic acid comprising a nucleotide sequence consisting of DD1.

In still another aspect, the present invention provides an isolated nucleic acid sequence consisting of DD2.

In still another aspect the present invention provides an isolated nucleic acid sequence consisting of DD3.

In still another aspect, the present invention provides a method for killing a breast cancer cell comprising contacting said cell with an amount of an agent selected from NRIF3 related molecules and derivatives thereof effective to kill said cell.

In still another aspect, the present invention provides a method for treating a patient suffering from breast cancer comprising administering to a patient in need of such treatment an amount of a nucleic acid encoding NRIF3 related molecule effective to kill said cancer cell.

These and other aspects of the present invention will be apparent to those of ordinary skill in the art in light of the present description claims and drawings.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 8. A model for NRIF3- or DD1-induced apoptosis. Breast cancer cells contain a specific death switch that can be selectively triggered by NRIF3 or its death domain DD1. Triggering of this switch by NRIF3 or DD1 leads to activation of caspase-2. Activated caspase-2 promotes MMP, which results in the release of AIF. The released AIF then mediates effector caspase-independent cell death (which is insensitive to zVAD-fmk). The anti-apoptotic factor Bcl-2 could inhibit this pathway by acting either upstream of caspase-2 (to prevent its activation) or downstream of caspase-2 (to prevent caspase-2-mediated changes in MMP) (24). It is also possible that activated caspase-2 can directly elicit cell death (dashed line) in addition to the depicted mitochondria-mediated pathway.

FIG. 11. (A-C) depicts the DNA sequence for (A) full-length NRIF3 (SEQ ID NO:1); (B) full-length EnL (SEQ ID NO:2); (C) full-length EnS (SEQ ID NO:3).

FIG. 12. (A-C) depicts the DNA sequence for (A) DD1 (SEQ ID NO:4); (B) DD2 (SEQ ID NO:5) and (C) DD3 (SEQ ID NO:6).

FIG. 13. Nucleotide (SEQ ID NO:7) and deduced amino acid sequences of NRIF3 (SEQ ID NO:8). Only part of the cDNA sequence is shown. A putative nuclear localization signal (KRKK) is underlined. The putative LxxLL motif is shown with a double underline. NRIF3 and the β3-endonexin long form (EnL) share 95% identity. They differ only in the C-terminus where the last 16 amino acids (dot underlined) in NRIF3 are replaced with 9 different amino acids (GQPQM-SQPL) in the β3-endonexin long form (SEQ ID NO:14). The short form of β3-endonexin consists of 111 amino acids and is 100% identical to the first 111 amino acids of NRIF3 or the β3-endonexin long form. The relative positions of DD1 (SEQ ID NO:1), DD2 (SEQ ID NO:12) and DD3 (SEQ ID NO:13) are shown with boxes.

DETAILED DESCRIPTION OF THE INVENTION

Figure 1A:
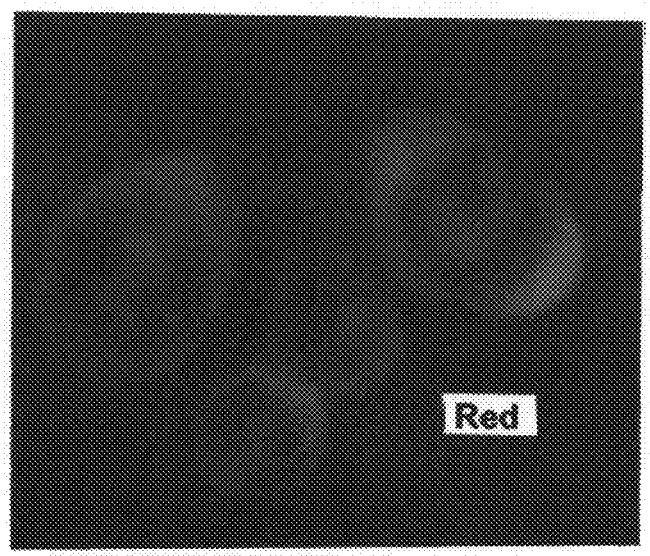
FIG. 1. (A and B) NRIF3 induces apoptosis in T-47D cells. (A) GFP-NRIF3 was expressed in T-47D cells by transient transfection. Twenty-four h later the green fluorescent cells were collected after sorting by flow-cytometry, and re-inoculated onto cover-slips. Cells were then analyzed for apoptosis by Annexin V staining (red). Control cells expressing GFP alone were negative for Annexin V staining (not shown). (B) Representative fluorescent micrographs of T-47D cells transfected with either GFPNLS or GFP-NRIF3. Cells were examined for apoptosis by TUNEL assay (red). (C) Quantitative presentation of the experiments described in (B). The percent of green fluorescent cells that were TUNEL positive were scored for T-47D cells transfected with either GFP-NRIF3 or GFPNLS.

Definitions:

The term about or approximately means within an acceptable error range for the particular value as determined by one of ordinary skill in the art, which will depend in part on how the value is measured or determined, i.e., the limitations of the measurement system, i.e., the degree of precision required for a particular purpose, such as a pharmaceutical formulation. For example, about can mean within 1 or more than 1 standard deviations, per the practice in the art. Alternatively, about can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

"NRIF3 related molecules" are defined as peptides consisting of full-length NRIF3, Death Domains 1-3 (DD1-DD3), EnS (endonexin short form) and EnL (endonexin long form) and nucleic acids encoding said peptides.

"NRIF3 derivatives" are defined as NRIF3 and related molecules (as defined above) that are either in the form of peptides that have been modified by linkage to known cell permeation peptide sequences derived from another protein or in the form of nucleic acids that encode the peptides. Examples of known cell-permeation peptide sequences include the hydrophobic region (h-region) of the signal peptide of Kaposi fibroblast growth factor (as described in Ye, H. et al., *Nature* 418:443-447, 2002; Yan Liu, X. et al., *J. Biol. Chem.* 275(22):16774-16778, 2000; Lin, Y. Z. et al., *J. Biol. Chem.* 270(24):14255-14258, 1995) or a cell-permeation sequence from the HIV tat protein (described in Goubaeva, F. et al., *J. Biol. Chem.* 278(22):19634-19641, 2003). The hydrophobic sequence derived from the Kaposi fibroblast growth factor signal sequence is as follows: AAVALLPAVL-LALLAP (SEQ ID NO:9).

The cell-permeation sequence derived from the HIV tat protein is as follows: GGGYGRKKRRQRRRG (SEQ ID NO:10).

Other derivatives are N-myristoylated versions of the NRIF3-related peptides. N-myristoylation is known to facilitate cell permeation by the modified peptide (as disclosed in Goubaeva, F. et al. supra, Eichholtz, T. et al., *J. Biol. Chem.* 268(3):1982-1986, 1993; Harris, T. E. et al., *Biochem. Biophys. Res. Commun.* 232(3):648-651, 1997).

"Sequence Conservative Variants" of a nucleotide sequence are those in which a change of one or more nucleotide in a given codon position results in no alteration in the amino acid encoded at that position.

The present invention is based on the unexpected discovery that NRIF3 related molecules and derivatives thereof selectively kill breast cancer cells by inducing apoptosis in the recipient cell. The human NRIF3 gene encodes several different proteins as a result of alternative splicing, including NRIF3, EnS (endonexin short form) and EnL (endonexin long form). Both EnS and EnL share extensive identity with NRIF3 at the amino acid level. EnS is identical to the first 111 amino acids of NRIF3. NRIF3 and EnL share 95% identity and differ only in the C-terminus where the last 16 amino acid residues in NRIF3 are replaced with 9 different amino acids in EnL (See FIG. 11).

NRIF3 related molecules and derivatives thereof can be used to treat mammals suffering from breast cancer. Such treatments would comprise administering to a patient in need of such treatment a breast-cancer-cell-killing effective amount of NRIF3 related molecules and derivatives thereof. For proteins or peptides or their derivatives, such effective amounts would broadly range between about 0.1 mg/kg body weight of the recipient and about 100 mg/kg body weight of the recipient. Such effective amounts can be optimized using various systems such as an in vitro cell-based testing system, which uses cultured breast cancer cell lines such as T-47D cells (available from the American Type Culture Collection, Manassas, Va. as ATCC Accession No. HTB-133), and into which NRIF3 related molecules and derivatives thereof are added at desired concentrations. The cells are then examined to see if the treated cells undergo apoptosis (by an appropriate apoptopic assay such as the TUNEL assay described below). In this way it is possible to determine the effective "killing" concentrations of the tested peptides. In addition, an animal-based testing system such as the well known nude mouse model (Brunner N. et al., Breast Cancer Res. Treat. 10(3): 229-242, 1987; Brodie A., Semin. Oncol. 30(4 Suppl 14):12-22, 2003) can be used to test the effective amounts of an NRIF3-related agent. Nude mice are naturally immunodeficient and can be inoculated to grow human breast cancer cells. Thus, the anti-tumor or therapeutic effect of the peptides and nucleic acids of the present invention can be studied. From such a study one can determine the effective doses that would suppress tumor growth and/or eradicate tumors, as well as possible toxicity information.

Pursuant to the present invention, NRIF3 related molecules and derivatives thereof may be administered to a mammal in need of such treatment in effective amounts to treat breast cancer parenterally, e.g., intramuscularly, intraperitoneally, subcutaneously and preferably intravenously or by direct injection into the tumor.

One of the advantages of using NRIF3 related molecules and derivatives thereof is that they only cause apoptosis in breast cancer cells. All of the other standard breast cancer treatments, i.e., chemotherapy and radiation cause extensive toxicity to normal cells of the recipient.

All of the peptides of the present invention are derived from NRIF3. These are full-length NRIF3, EnL, EnS and the common death domains shared by all three of them (DD1, amino acid residues 20-50; DD2, amino acid residues 47-86, as well as DD3 amino acid residues 112-177).

The NRIF3 related molecules can be obtained using techniques well known to those of ordinary skill in the arts after expression of the constructs described herein below in the Materials and Methods section of the Examples. The peptides can be obtained after expression in suitable eukaryotic or prokaryotic cells well known to those of ordinary skill in the art, or by chemical synthesis. Expressed peptides can be purified directly using conventional chromatography techniques, or purified via suitable affinity chromatography when they are expressed as a fusion to an appropriate affinity tag (as described in Current Protocols in Protein Science, and Current Protocols in Molecular Biology; John Wiley & Sons). In all cases, a further purification using HPLC can also be applied. The methodology involved for producing such peptides is generally known in the art.

FIG. 11 depicts the DNA sequence for full-length NRIF3 (SEQ ID NO:1), full-length EnL (SEQ ID NO:2) and full-length EnS (SEQ ID NO:3). FIG. 12 depicts the DNA sequence coding for DD1 (SEQ ID NO:4), DD2 (SEQ ID NO:5) and DD3 (SEQ ID NO:6). FIG. 13 depicts the DNA (SEQ ID NO:7) and protein sequence of full-length NIRF3 (SEQ ID NO:8) and shows the relative positions of DD1 (SEQ ID NO:11), DD2 (SEQ ID NO:12), and DD3 (SEQ ID NO:13).

The present invention also includes sequence conservative variants of the NRIF3 related molecules of the present invention as defined above.

```
Amino Acid Sequence of Death Domain 1 (DD1):
                                  (SEQ ID NO: 11)
P S K I T R K K S V I T Y S P T T G T C Q M S L
FASPTSS Amino Acid Sequence of Death Domain 2 (DD2):
                                  (SEQ ID NO: 12)
P T S S E E Q K H R N G L S N E K R K K L N H P
SLTESKESTTKDNDEF Sequence of Death Domain 3 (DD3):
                                  (SEQ ID NO: 13)
A L E G S R E L E N L I G I S C A S H F L K R E
M Q K T K E L M T K V N K Q K L F E K S T G L P
HKASRHLDSYEFLKAILN
```

Another embodiment of the present invention is directed to pharmaceutical formulations and dosage forms for treating patients suffering from breast cancer. When formulated in a pharmaceutical formulation, NRIF3 related molecules and/or derivatives thereof can be admixed with a pharmaceutically acceptable carrier or excipient. The phrase "pharmaceutically acceptable" refers to molecular entities and compositions that are "generally regarded as safe", e.g., that are physiologically tolerable and do not typically produce an allergic or similar untoward reaction such as gastric upset, dizziness and the like, when administered to a human. Preferably, as used herein, the term "pharmaceutically acceptable" means approved by a regulatory agency of the Federal or a State government or listed in the U.S. Pharmacopeia or other generally recognized pharmacopeia for use in animals, and, more particularly, in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The pharmaceutical formulation of the present invention need not contain an amount effective for treating breast cancer as such effective amount can be attained by administering a plurality of the formulations.

In an alternative preferred embodiment of the present invention, the breast cancer killing properties of the NRIF3 related molecules can be utilized in a gene therapy format. For example, instead of administering a therapeutic peptide, the corresponding nucleic acid(s) (e.g., DNA), can be introduced into breast cancer cells. In this way, the breast cancer cells would synthesize the peptides which would result in the death of the cancer cell. The Examples below demonstrate that this approach is effective in killing the recipient breast cancer cell.

In this embodiment, effective amounts of the NRIF3 related molecules of the present invention effective for killing breast cancer cells are synthesized using the DNA encoding such molecules. The DNA can be administered in a viral vector, a DNA plasmid or as "naked" DNA as described further below. The effective amounts can be determined by routine experimentation using for example, the nude mouse model in combination with known human breast cancer cell lines.

The nucleic acids encoding the NRIF3 related molecules of the present invention can be delivered to cancer cells in a retroviral vector, e.g., as described in Anderson et al., U.S. Pat. No. 5,399,346; Mann et al., Cell 1983, 33:153; U.S. Pat. Nos. 4,650,764, 4,980,289, and 5,124,263; Markowitz et al., J. Virol. 1988, 62:1120; Temin et al., U.S. Pat. No.; EP 453242, EP178220; Bernstein et al. Genet. Eng. 1985, 7:235; McCormick, BioTechnology 1985, 3:689; PCT; and Kuo et al., Blood 1993, 82:845. These vectors can be constructed from different types of retrovirus, such as, HIV; MoMuLV ("murine Moloney leukaemia virus"); MSV ("murine Moloney sarcoma virus"); HaSV ("Harvey sarcoma virus"); SNV ("spleen necrosis virus"); RSV ("Rous sarcoma virus") and Friend virus. Suitable packaging cell lines have been described in the prior art, in particular the cell line PA317 (U.S. Pat. No. 4,861,719); the PsiCRIP cell line (PCT Publication No. WO 90/02806) and the GP+envAm-12 cell line (PCT Publication No. WO 89/07150). Retrovirus vectors can also be introduced by DNA viruses, which permits one cycle of retroviral replication and amplifies transfection efficiency (see PCT Publication Nos. WO 95/22617, WO 95/26411, WO 96/39036, WO 97/19182).

DNA viral vectors, including an attenuated or defective DNA virus, such as but not limited to herpes simplex virus (HSV), papillomavirus, Epstein Barr virus (EBV), adenovirus, adeno-associated virus (AAV), and the like can also be used to deliver the NRIF3 related molecules of the present invention. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al., Molec. Cell. Neurosci. 1991, 2:320-330), defective herpes virus vector lacking a glyco-protein L gene (Patent Publication RD 371005 A), or other defective herpes virus vectors (PCT Publication Nos. WO 94/21807 and WO 92/05263); an attenuated adenovirus vector, such as the vector described by Stratford-Perricaudet et al. (J. Clin. Invest. 1992, 90:626-630; see also La Salle et al., Science 1993, 259:988-990; various replication defective adenovirus and minimum adenovirus vectors have been described in PCT Publication Nos. WO 94/26914, WO 95/02697, WO 94/28938, WO 94/28152, WO 94/12649, WO 95/02697, and WO 96/22378); and a defective adeno-associated virus vector (Samulski et al., J. Virol. 1987, 61:3096-3101; Samulski et al., J. Virol. 1989, 63:3822-3828; Lebkowski et al., Mol. Cell. Biol. 1988, 8:3988-3996; PCT Publication Nos. WO 91/18088 and WO 93/09239; U.S. Pat. Nos. 4,797,368 and 5,139,941; European Publication No. EP 488 528).

Various companies produce viral vectors commercially, including but by no means limited to Avigen, Inc. (Alameda, Calif.; AAV vectors), Cell Genesys (Foster City, Calif.; retroviral, adenoviral, AAV vectors, and lentiviral vectors), Clontech (retroviral and baculoviral vectors), Genovo, Inc. (Sharon Hill, Pa.; adenoviral and AAV vectors), Genvec (adenoviral vectors), IntroGene (Leiden, Netherlands; adenoviral vectors), Molecular Medicine (retroviral, adenoviral, AAV, and herpes viral vectors), Norgen (adenoviral vectors), Oxford BioMedica (Oxford, United Kingdom; lentiviral vectors), and Transgene (Strasbourg, France; adenoviral, vaccinia, retroviral, and lentiviral vectors).

In another embodiment, the vector can be non-viral. Such vectors include "naked" DNA, and transfection facilitating agents (peptides, polymers, etc.). Synthetic cationic lipids can be used to prepare liposomes for transfection of a gene encoding a desired molecule (Felgner, et al., Proc. Natl. Acad. Sci. U.S.A. 1987, 84:7413-7417; Felgner and Ringold, Science 1989, 337:387-388; see Mackey, et al., Proc. Natl. Acad. Sci. U.S.A. 1988, 85:8027-8031; Ulmer et al., Science 1993, 259:1745-1748). Useful lipid compounds and compositions for transfer of nucleic acids are described in International Patent Publications WO95/18863 and WO96/17823, and in U.S. Pat. No. 5,459,127. Lipids may be chemically coupled to other molecules for the purpose of targeting (see Mackey, et. al., supra). Targeted peptides, e.g., hormones and proteins such as antibodies, or non-peptide molecules could be coupled to liposomes chemically. Other molecules are also useful for facilitating transfection of a nucleic acid in vivo, such as a cationic oligopeptide (e.g., International Patent Publication WO95/21931), peptides derived from DNA binding proteins (e.g., International Patent Publication WO96/25508), or a cationic polymer (e.g., International Patent Publication WO95/21931).

In another embodiment the vector comprises a naked DNA plasmid. Naked DNA vectors for gene therapy can be introduced into the desired host cells by methods known in the art, e.g., electroporation, microinjection, cell fusion, DEAE dextran, calcium phosphate precipitation, use of a gene gun, or use of a DNA vector transporter (see, e.g., Wu et al., J. Biol. Chem. 1992, 267:963-967; Wu and Wu, J. Biol. Chem. 1988, 263:14621-14624; Hartmut et al., Canadian Patent Application No. 2,012,311, filed Mar. 15, 1990; Williams et al., Proc. Natl. Acad. Sci. USA 1991, 88:2726-2730). Receptor-mediated DNA delivery approaches can also be used (Curiel et al., Hum. Gene Ther. 1992, 3:147-154; Wu and Wu, J. Biol. Chem. 1987, 262:4429-4432). U.S. Pat. Nos. 5,580,859 and 5,589,466 disclose delivery of exogenous DNA sequences, free of transfection facilitating agents, in a mammal.

The present invention is described below in working examples which are intended to further describe the invention without limiting its scope.

EXAMPLE 1

In the examples below the following materials and methods were used.

Plasmids. Plasmids expressing GFP-NRIF3, GFP-EnS, GFP-EnL, the GFP control, wild type NRIF3, Gal4-DD1, Gal4-DD3 and the Gal4 control, have been described (28, 29). The GFPNLS vector expresses nuclear-localized GFP, where the NLS is derived from the SV40 T antigen (1). Constructs expressing GFP- or GFPNLS-fusion of various regions of NRIF3 were generated by PCR-based cloning. Briefly, DNA fragments encoding a desired NRIF3 region was produced by PCR amplification, digested with XhoI and Acc65I, and cloned into either the original GFP vector (for regions corresponding to residues 1-86 and 20-86) or a GFPNLS vector (for wild type DD1 and the S28A mutant DD1, as well as DD2) digested with the same pair of enzymes. All GFP-fusion constructs were confirmed by sequence analysis. The AIF-GFP plasmid was kindly provided by Dr. Guido Kroemer (31). Vectors expressing Bcl-2 and Bcl-xL were gifts from Dr. Honglin Li.

Cell culture and transfection conditions. All breast cancer cell lines were maintained in DMEM (GIBCO-BRL, Life Technologies) supplemented with 10% fetal bovine serum (FBS). Other cells were cultured in DMEM supplemented with either 10% FBS or 10% Hyclone defined/supplemented bovine calf serum. For most of the transient transfections, T-47D cells were plated at a density of $3\times10^4$ cells/well on coverslips in 24-well tissue culture plates. About 20 h later, the cells were transfected with indicated plasmid(s) by Genefect transfection reagent (Molecula, USA) according to manufacturer's protocol. Generally, the amount of plasmids used in transfections was the following: GFP or GFP-fusion 300-500 ng, Bcl-2 or Bcl-xL 1-1.5 µg, AIF-GFP 500 ng, Gal4-DD1, GA14-DD3 or Gal4 control 0.5-1 µg. After transfection, cells were incubated in DMEM/10% FBS medium for 5 h to 24 h before being harvested and processed for appropriate analyses. Transient transfection of other breast cancer cell lines were carried out similarly, except that the transfection reagent used was Lipofectamine 2000 (Life technologies). All other cells were transfected using Geneporter 2 (Gene Therapy Systems). When indicated, the following compounds were included in the medium: all-trans retinoic acid (100 nM), etopside (100 µM), zVAD-fmk (100 µM), zVDVAD-fmk (20 µM), TNFα (10 ng/ml) and cycloheximide (10 µg/ml).

Flow cytometry and cell sorting analysis. Cells transfected with an appropriate GFP construct were processed for flow cytometry analysis as previously described (2). Flow cytometric analysis for GFP and propidium iodide was performed using four-color FACscan (Becton-Dickinson Immunocytometry System, San Jose, Calif., USA). GFP positive or negative cells were analyzed for changes in cell cycle distribution. For re-inoculation studies, cells were plated at a density of $3\times10^6$ cells/plate in a 100 cm$^2$ tissue culture plate and transfected with 50 µg of indicated GFP or GFP-fusion constructs using Genefect. About 24 h after transfection, cells were harvested and sorted by flow cytometry. GFP positive or negative cells were collected, and re-plated at $3\times10^4$ cells/well in 24-well plates. Cells were monitored over a period of 48-72 h for attachment, growth, and morphological changes. In some cases, the collected cells were re-plated onto coverslips and subsequently processed for Annexin V staining.

siRNA studies. A small interference RNA (siRNA) duplex that efficiently silences human caspase-2 expression has been previously described (27), and was purchased from Dharmacon. The siRNA was dissolved at 20 µmol/µl in H$_2$O. T-47D cells were plated at the density of $1.5\times10^5$ cells/well in 6-well plates the day before being transfected with siRNA. Transfection was carried out using Oligofectamine (Invitrogen), with 12 µl of dissolved siRNA and 12 µl of Oligofectamine reagent. Cells were fed with additional DMEM/10% FBS the second day, and harvested about 42 h after siRNA transfection. Mock-transfected cells were treated similarly but did not receive caspase-2 siRNA. The harvested cells were then re-plated on cover-slips in 24-well plates as described earlier, and incubated for a few hours to let attachment occur. Cells were then transfected with the indicated GFP or GFP-fusion vectors as described earlier or treated with etoposide (100 µM). Cells were harvested about 20-24 h later and processed for appropriate assays. To document caspase-2 knock down, total lysates from siRNA transfected or control cells were quantified for protein concentrations. Equal amount of proteins were then subjected to SDS-PAGE, followed by Western analysis using a monoclonal antibody against caspase-2 (11B4, from Alexis).

Apoptosis assays. Cells plated on cover-slips in 24-well tissue culture plates were transfected and/or treated with appropriate compounds as indicated. Generally, cells were harvested within 20-24 h and processed for TUNEL and/or Annexin V assays. For Annexin V assay, cells were washed 3× with PBS and assayed using ApoAlert Nitric Oxide/Annexin V Dual Sensor Kit (BD Biosciences, USA) according to manufacturer's protocol. Cells were then mounted on slides using Dako Fluorescent Mounting Media, (DAKO Corporation, USA) and examined by fluorescent microscopy. For TUNEL assays, cells were washed 3× with PBS, fixed in 3.7% formaldehyde, and assayed using the "In Situ Cell Death Detection Kit" (TMR red) (Roche Diagnostics GmbH, Germany) according to manufacturer's protocol. In some cases, cells were also stained with Hoechst dye to visualize nuclei. Cells were then mounted on slides and examined by fluorescent microscopy. For quantitative analysis, fields consisting of at least several hundred cells were scanned, and a number of representative fields were photographed using GFP and rhodamine filters. Green and red cells from the same field were then counted. Generally, about one hundred of total green cells were counted for each data point. The percent of green cells counted that are also red were then calculated.

EXAMPLE 1

NRIF3 induces rapid and profound cell death in T-47D cells. We previously identified NRIF3 as a co-activator for certain members of the nuclear hormone receptor superfamily, including TR and RXR (28, 29). A unique feature of RXR is that it serves as the common heterodimeric partner for many other members of the nuclear receptor superfamily (33). Thus, a heterodimer composed of the retinoic acid receptor (RAR) and RXR is the functional unit that transduces retinoid signaling in vivo (21, 22). Retinoid signaling plays important roles in both development and homeostasis (21, 22). In addition, retinoids are known to inhibit the proliferation of certain breast cancer cells (2, 15), although the underlying molecular mechanism(s) have not been fully defined.

Our identification of NRIF3 as a co-activator for RXR prompted us to test whether NRIF3 would enhance the antiproliferative effect of retinoids in responsive breast cancer cells. We and others have previously shown that retinoid treatment inhibits the proliferation of T-47D and MCF-7 breast cancer cell lines (2, 39, 43). This results in an increase in distribution of cells in the G0-G1 phase of the cell cycle and a concomitant decrease in the number of cells in S phase (2). To test the effect of NRIF3, we transfected T-47D cells with a vector expressing GFP or GFP-NRIF3 and incubated the cells with or without all-trans-retinoic acid (tRA). Green fluorescent and non-green cells were then sorted by flow cytometry and analyzed for cell cycle distribution. Intriguingly, we found that expression of GFP-NRIF3 (but not the GFP control) was sufficient to inhibit the proliferation of T-47D cells, whether or not the cells were incubated with tRA (data not shown). This result suggested that NRIF3 mediates an antiproliferative effect on T-47D cells independent of retinoid treatment.

To examine this further, we collected sorted green fluorescent cells expressing either GFP-NRIF3 or GFP and re-plated them in culture dishes to monitor cell growth. While GFP expressing cells attached and grew normally, cells expressing GFP-NRIF3 attached to the dish inefficiently and failed to divide. Microscopy examination revealed that the GFP-NRIF3 expressing cells displayed morphological changes suggestive of apoptosis (rounded-up cell shape and cytoplasmic shrinkage). Thus, we examined these cells for apoptosis using an Annexin V assay (19, 49), and found that virtually all cells expressing GFP-NRIF3 were positive for Annexin V staining while the control cells expressing GFP were negative (FIG. 1A, and data not shown).

Figure 1B:
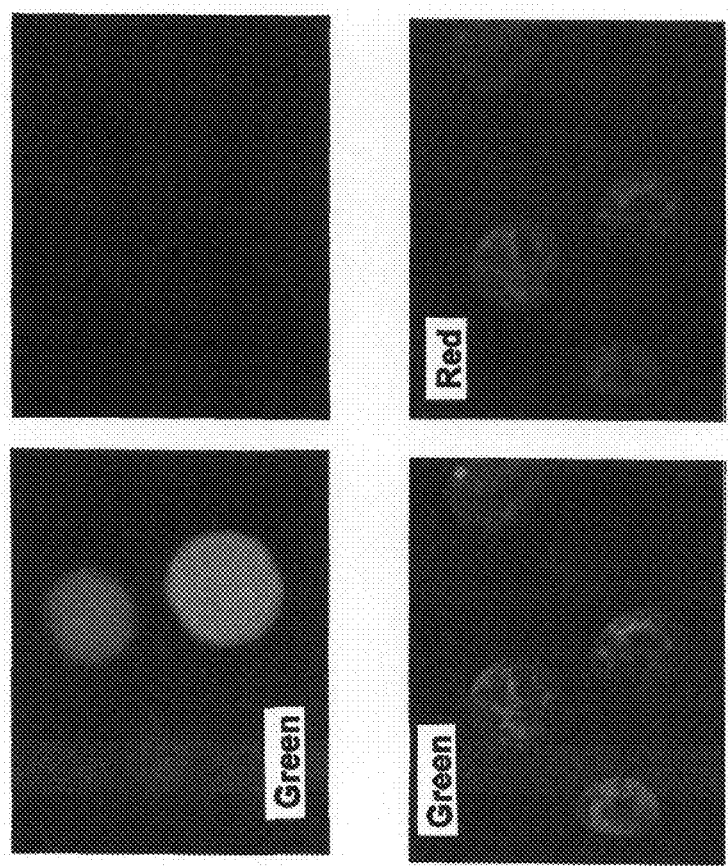
Figure 1C:
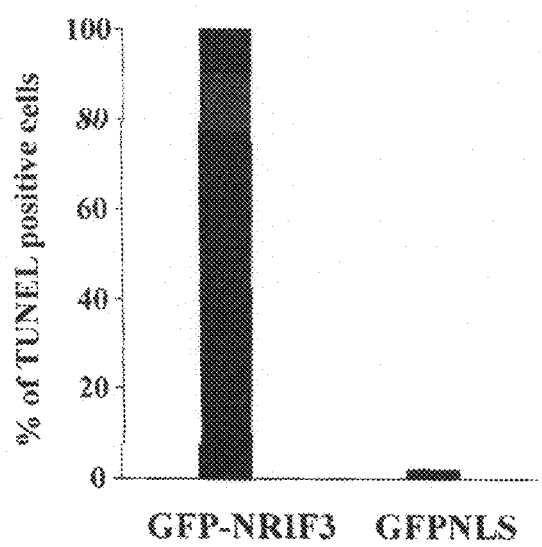

To further confirm that NRIF3 induces apoptosis, T-47D cells expressing GFP-NRIF3 or GFP fused to a nuclear localization signal (GFPNLS) were examined by a TUNEL assay (16). GFPNLS was included as a control since NRIF3 is a nuclear protein (28). Initial experiments suggested that the number of green fluorescent cells is maximal 20 to 24 h after transfection. Therefore, in most of our studies, a TUNEL assay was carried out about 20 h after transfection. We found that GFP-NRIF3 expressing cells were TUNEL positive while GFPNLS expressing cells were TUNEL negative (FIG. 1B). Quantitative analyses revealed that nearly 100% of GFP-NRIF3 expressing cells were TUNEL positive within 24 h after transfection, compared with little or no TUNEL reaction for GFPNLS expressing cells (FIG. 1C). To rule out the possibility that cell death mediated by GFP-NRIF3 results from the fusion of GFP and NRIF3 instead of NRIF3 itself, we also transfected T-47D cells with a vector expressing full-length wild-type NRIF3 (not as a GFP fusion) and found that the transfected cells also underwent apoptosis (data not shown). Taken together, our results indicate that expression of NRIF3 induces rapid and profound death in T-47D cells via apoptosis or an apoptosis-like process.

EXAMPLE 2

Figure 2A:
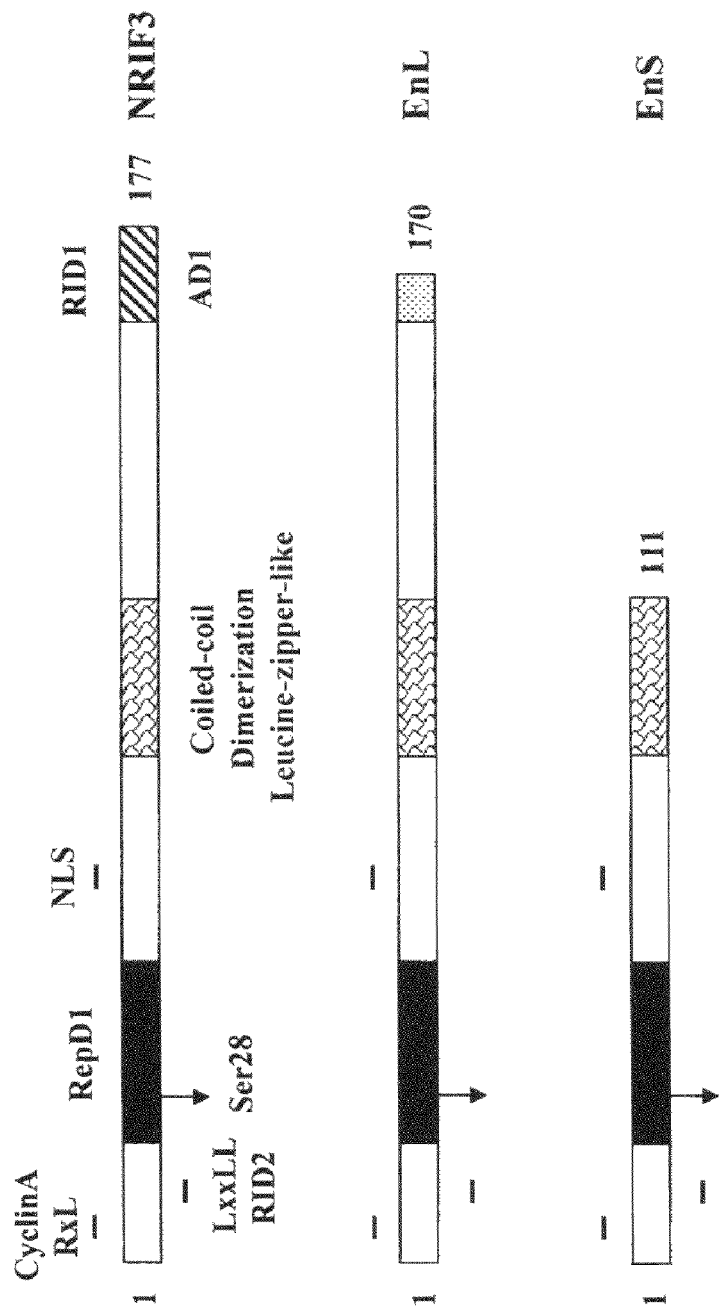
FIG. 2. (A and B) Cell death induced by EnS and EnL. (A) Domain organization and functional motifs in NRIF3, EnS, and EnL. NRIF3 contains two nuclear receptor interaction domains (RID1, residues 162-177; and RID2, residues 9-13) (28, 29). An activation domain (ADI) co-resides with RID1. A transrepression domain (RepD1) maps to residues 20-50 (29). Also shown are a cyclin A binding motif RxL (residues 6-8), a coiled-coil dimerization domain (residues 86-112) that contains a leucine-zipper-like motif, and a nuclear localization signal (NLS, residues 63-66) (29, 36). Ser28 in RepD1 is marked by an arrow. EnS and EnL share extensive identities with NRIF3 and contain the same domains/motifs except for RID1/AD 1. (B) Representative fluorescent micrographs of T-47D cells transfected with either GFP-EnS or GFP-EnL. Cells were examined for apoptosis by TUNEL assay (red).
Figure 2B:
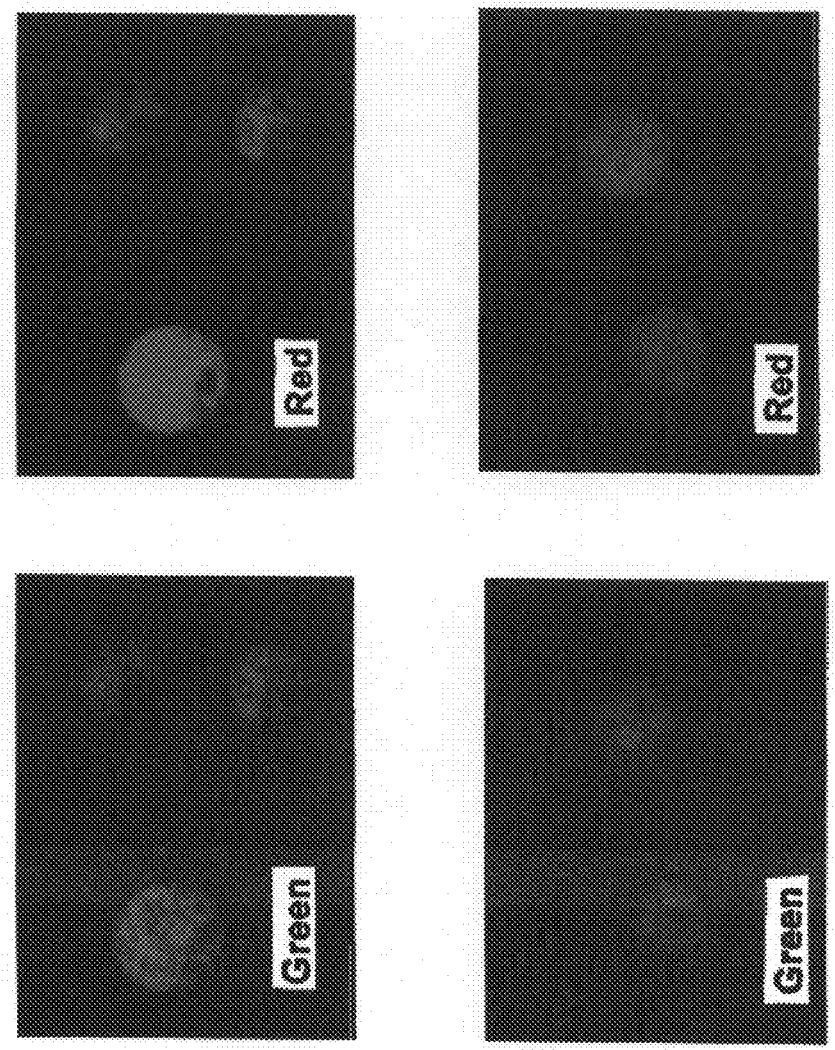

Other members of the NRIF3 family induce apoptosis in T-47D cells. The human NRIF3 gene encodes several different proteins as a result of alternative splicing, including NRIF3, EnS (endonexin short form), and EnL (endonexin long form) (28, 29, 44). Both EnS and EnL share extensive identity with NRIF3 at the amino acid level (28, 29) (FIG. 2A). EnS is identical to the first 111 amino acids of NRIF3, and thus can be viewed as a naturally occurring truncation of NRIF3. Like NRIF3, EnS and EnL are primarily nuclear-localized, and together with NRIF3 constitute a new family of transcriptional coregulators (29). Given the similarity among the NRIF3 family members, we asked whether EnS and EnL also induce apoptosis in T-47D cells. To this end, T-47D cells were transfected with vectors expressing GFP-EnS or GFP-EnL, and 20 h later, were analyzed for expression of the GFP-fusion proteins and for apoptosis. We found that expression of GFP-EnS or GFP-EnL resulted in profound apoptosis (nearly 100% of green cells were TUNEL positive), indicating that the N-terminal portion of NRIF3 (residues 1-111) is sufficient to induce death in T-47D cells (FIG. 2B and data not shown).

EXAMPLE 3

NRIF3 contains a novel death domain (DD1). The region comprising the first 111 amino acids of NRIF3 (equivalent to EnS), which is sufficient to induce apoptosis, contains a number of structural and functional features identified in previous studies (29, 36). These include a coiled-coil domain (residues 84-112) that mediates protein-protein interactions, a putative nuclear localization signal (residues 63-66), a transrepression domain (residues 20-50, RepD1), an LxxLL motif (residues 9-13) that plays a role in interaction with certain nuclear receptors, and an RxL motif (residues 6-8) that binds cyclin A and mediates interaction with cyclin A/Cdk2 (see FIG. 2A). To test whether any of these known domains/motifs are required for NRIF3-mediated apoptosis and to further map the functional death domain in NRIF3, we generated a series of GFP-vectors expressing various regions of the N-terminal 111 amino acids of NRIF3. These GFP-fusion constructs were then individually expressed in T-47D cells to examine induction of apoptosis (FIG. 3A).

Figure 3A:
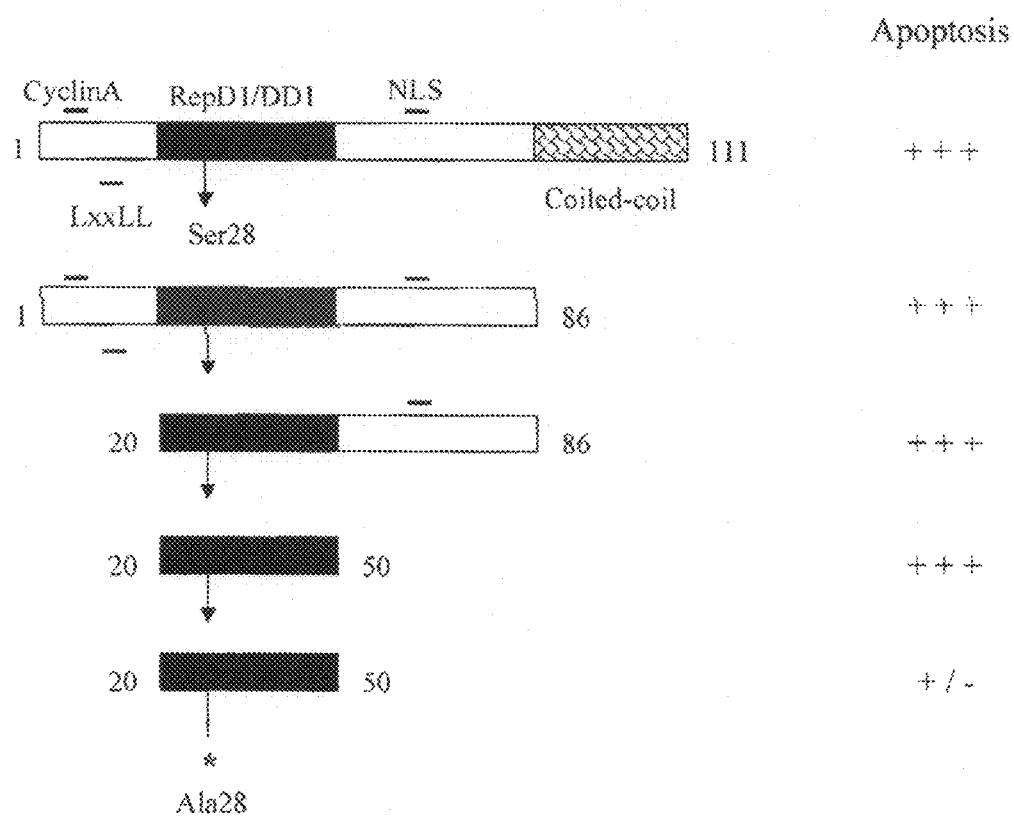
FIG. 3. (A-C) NRIF3 contains a novel death domain (DD1). (A) T-47D cells were transfected with each of the indicated constructs expressing various regions of NRIF3 fused to GFP or GFPNLS. Ser28 in wild type DD1 is marked by an arrow, while Ala28 in the mutant DD1 is marked by a star. These regions were expressed either as a GFP-fusion, or for those lacking an intrinsic NLS, as a GFPNLS-fusion. Green fluorescent cells were scored for apoptosis by TUNEL assay or Annexin V staining or both. "+++" indicates profound cell death, where nearly 100% of green cells displayed positive staining for TUNEL and/or Annexin V, while "–" indicates no apoptosis (less than 2% positive). (B) Representative fluorescent micrographs of T-47D cells transfected with GFPNLS, wild type (WT) GFPNLS-DD1 (residues 20-50 of NRIF3), or the GFPNLS-DD1 mutant (S28A). Cells were examined for apoptosis by TUNEL assay (red). (C) The Ser28 to Ala mutation severely compromises the apoptogenic function of DD1. The percent of green fluorescent cells that were TUNEL positive were scored for T-47D cells transfected with either wild type GFPNLS-DD1 or the mutant GFPNLS-DD1S28A.
Figure 3B:
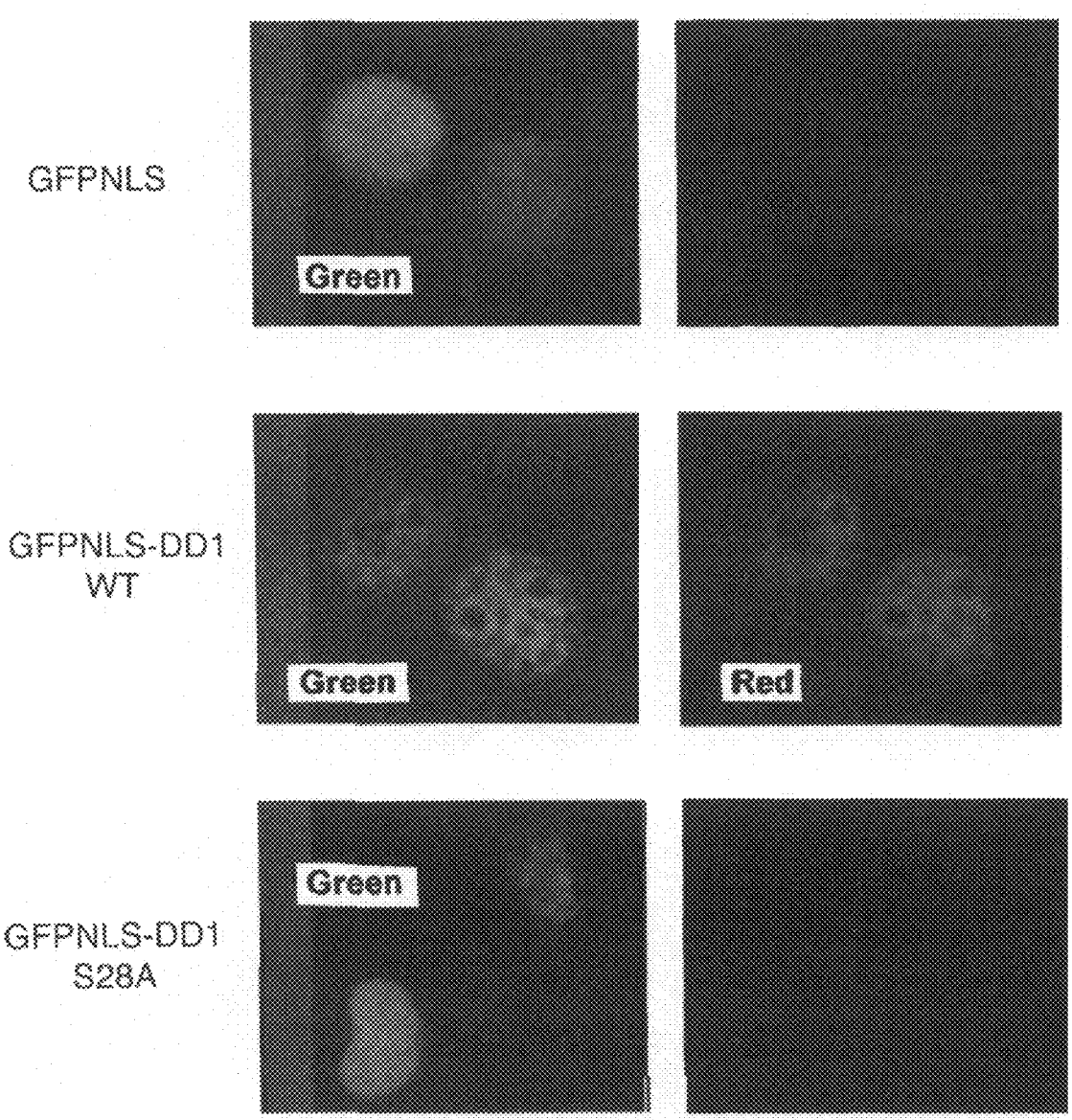

Expression of regions comprising amino acids 1-86 or 20-86 were found to efficiently induce apoptosis in T-47D cells, indicating that the coiled-coil domain (residues 84-112), the cyclin A binding motif (residues 6-8), and the LxxLL motif (residues 9-13) are all dispensable for the apoptogenic effect of NRIF3 (FIG. 3A). The region comprising residues 20-86 of NRIF3 contains a previously identified transrepression domain RepD1 (residues 20-50) (29). Thus, we further examined RepD1 and found that its expression efficiently induced death in T-47D cells (FIGS. 3A and 3B). Taken together, these results identify a novel death domain (residues 20-50, designated here as DD1) in the NRIF3 family, which interestingly, co-resides with RepD1 (FIG. 3A). We detected no homology for DD1 with other known death domains in the database.

Our previous study in other cell lines identified a putative phosphorylation site (Ser28) in RepD1 (29). Phosphorylation of Ser28 appears to be essential for the transcriptional repression function of RepD1 as a change of Ser28 to Ala (S28A) abolishes repression (29). To test the potential role of Ser28 phosphorylation in apoptosis, we examined the DD1/RepD1 S28A mutant and found that this mutation markedly reduced the ability of DD1 to induce apoptosis in T-47D cells (FIGS. 3B and 3C), suggesting that phosphorylation of Ser28 in vivo is important for the apoptogenic function of DD1.

EXAMPLE 4

NRIF3- and DD1-mediated apoptosis is insensitive to zVAD-fmk. Since activation of caspases is central to many cell death programs, we tested whether zVAD-fmk, a broad-spectrum irreversible caspase inhibitor (14, 47), has any effect on NRIF3- and DD1-mediated apoptosis in T-47D cells. For these studies, T-47D cells were incubated with 100 uM zVAD-fmk prior to and after transfection with appropriate GFP fusion constructs. We found that zVAD-fmk did not inhibit apoptosis mediated by GFP-NRIF3 or GFPNLS-DD1 (FIGS. 4A and 4B). zVAD-fmk alone did not cause cell death (data not shown). The same dose of zVAD-fmk was found to significantly inhibit apoptosis of HeLa cells treated with TNFα and cycloheximide (data not shown), where the apoptotic process is dependent on caspase-8 and downstream effector caspase(s) (10, 18, 34). Taken together, our results indicate that NRIF3- and DD1-mediated apoptosis in T-47D is insensitive to zVAD-fmk.

EXAMPLE 5

Figure 5A:
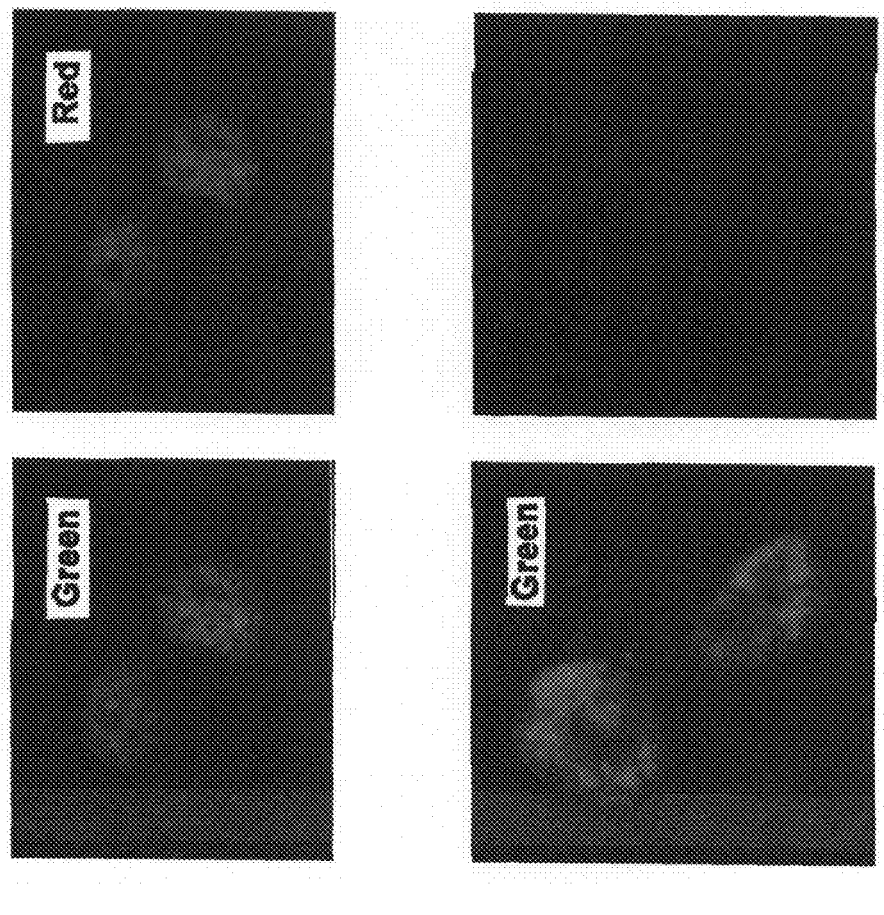
FIG. 5. (A and B) DD1-mediated cell death involves MMP. (A) Representative fluorescent micrographs of T-47D cells transfected with either GFPNLS-DD1, or GFPNLS-DD1 and Bcl-2. Cells were examined for apoptosis by TUNEL assay (red). (B) Quantitative presentation of the experiments in (A). The percent of green fluorescent cells that were TUNEL positive were scored for T-47D cells transfected with either GFPNLS-DD1 or with GFPNLS-DD1 and Bcl-2. (C) T-47D cells were transfected to express AIF-GFP along with either a control vector or a vector expressing DD1. Approximately 5 h after transfection the cells were fixed and subjected to TUNEL assay. The cells were then examined by fluorescent microscopy for sub-cellular location of AIF-GFP (green) and for apoptosis (red). Nuclei were stained with Hoechst (blue). Representative fluorescent micrographs of cells transfected with the control vector or DD1 are compared.
Figure 5B:
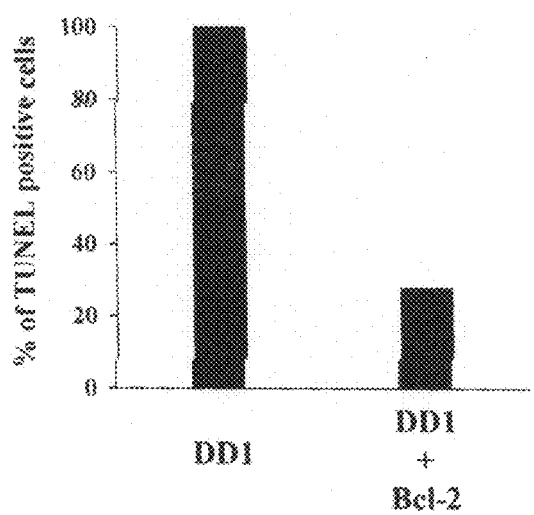

Role of mitochondria in DD1-mediated cell death. MMP is a critical event in the intrinsic apoptosis pathway as it results in the release of a number of death-promoting molecules such as cytochrome-c and AIF (38, 50). Members of the Bcl-2 family regulate mitochondria-mediated cell death by controlling MMP, which is determined by the relative balance of pro-apoptotic (e.g. Bak, Bax, Bad and Bid) and anti-apoptotic (e.g. Bcl-2 and Bcl-xL) members of the family (3, 7). To assess whether DD1-induced cell death involves a mitochondria-mediated pathway, we examined whether the apoptogenic effect of DD1 was inhibited by Bcl-2. We found that co-expression of Bcl-2 significantly inhibited DD1-mediated apoptosis in T-47D cells (FIGS. 5A and 5B). Similar inhibition was found with Bcl-xL (data not shown). These results suggest that MMP plays a role in DD1-induced apoptosis.

Figure 5C:
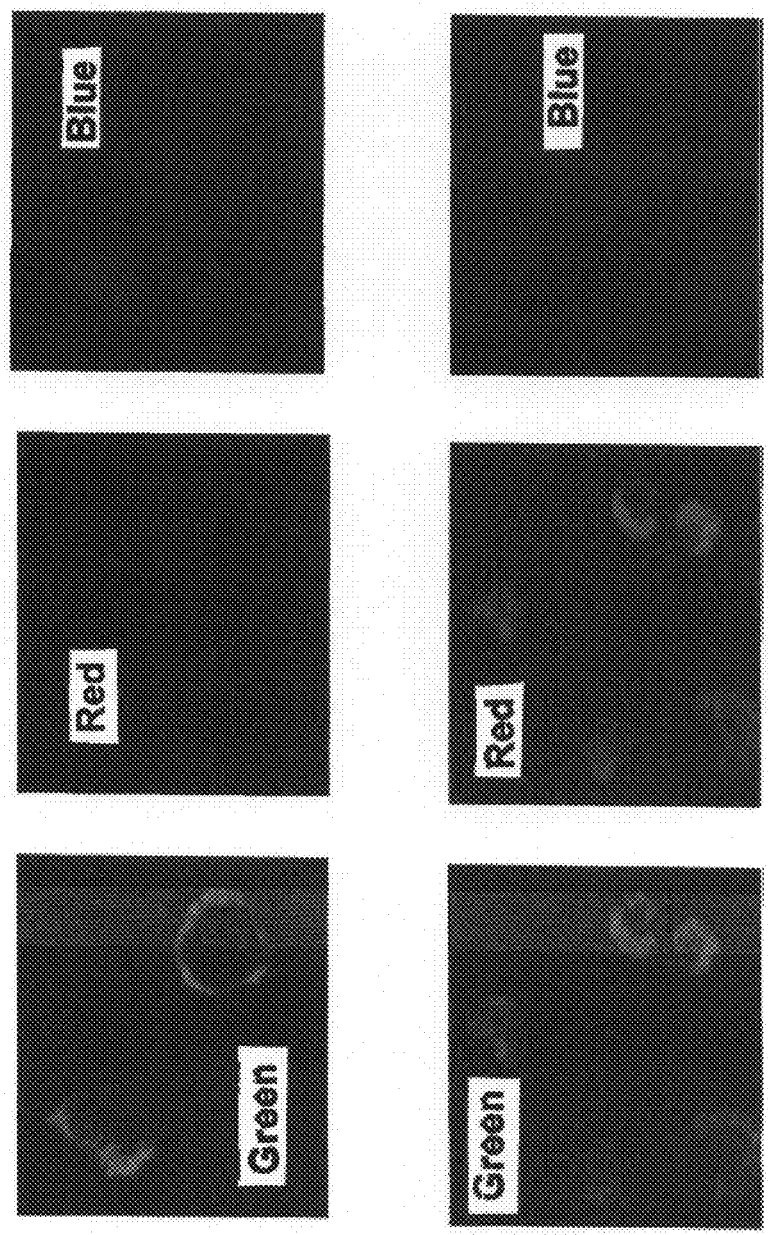

To further document that DD1 induces MMP, we examined whether AIF is translocated from the mitochondria to the nucleus during DD1-mediated cell death, using a vector expressing AIF-GFP (31). Consistent with a previous study (31), expression of AIF-GFP alone resulted in a mitochondrial pattern of distribution (FIG. 5C). Interestingly, co-expression of DD1 resulted in the translocation of AIF-GFP from mitochondria to the nucleus as early as 5 h after transfection (FIG. 5C). Cells containing nuclear localized AIF-GFP also underwent apoptosis as assessed by TUNEL assay (FIG. 5C). Taken together, our results in FIG. 5 support a model whereby the DD1 of NRIF3 promotes apoptosis in T-47D cells through a mitochondria-mediated pathway that is regulated by Bcl-2 and involves the translocation of AIF. Since AIF promotes effector caspase-independent apoptosis (8, 38), its translocation during DD-induced cell death is consistent with our earlier finding that this death program is insensitive to zVAD-fmk.

EXAMPLE 6

Requirement for caspase-2 in DD1-mediated apoptosis. A number of recent studies suggest an important role for caspase-2 in the intrinsic (stress-induced) apoptosis pathway in certain cell types where its activity is required for promoting MMP (17, 24, 27, 42). Although caspase-2 was reported to be present in a number of cellular compartments (for a review, see reference 48), recent studies suggest that it is mainly a nuclear protein and that it can trigger MMP and apoptosis from the nucleus without redistribution to the cytoplasm (4, 12, 37, 45). The fact that members of the NRIF3 family are nuclear proteins raises the possibility that the DD1 of NRIF3 might act through activation of nuclear localized caspase-2. The finding that DD1-induced cell death is not inhibited by zVAD-fmk does not exclude a potential role for caspase-2, as caspase-2 is several orders of magnitude more resistant to zVAD-fmk than other caspases (14).

Figure 6B:
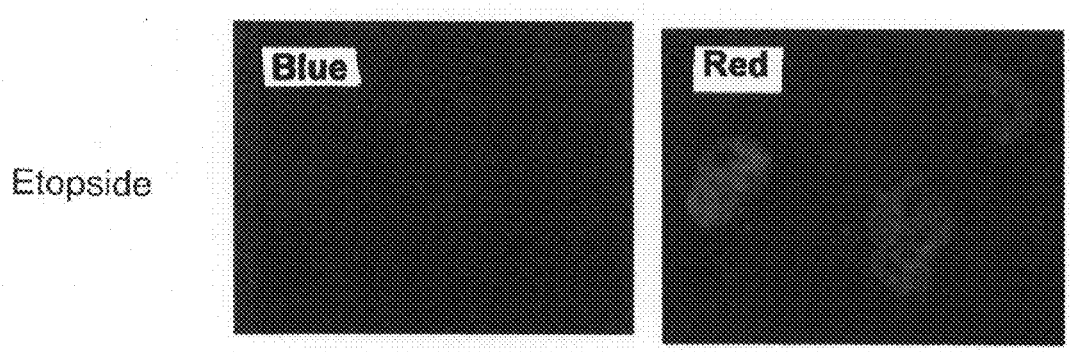
FIG. 6. (A-C) Requirement for caspase-2 in DD1-mediated apoptosis. (A) T-47D cells pre-treated with caspase-2 siRNA or mock-treated control cells were transfected with GFPNLS-DD1. Cells were examined for apoptosis by TUNEL assay (red). Representative fluorescent micrographs of siRNA-treated or mock-treated cells are compared. (B) T-47D cells pre-treated with caspase-2 siRNA or mock-treated control cells were incubated with etoposide. Cells were examined for apoptosis by TUNEL assay (red) while the nuclei were visualized by Hoechst staining (blue). Representative fluorescent micrographs are shown for the siRNA treated cells. Similar result is observed for the mock-treated control cells (not shown). (C) Quantitative presentation of the experiments in (A). The percent of green fluorescent cells (expressing GFP-NLS-DD1) that were TUNEL positive were scored for cells pre-treated with caspase-2 siRNA or for mock-treated control cells.
Figure 6C:
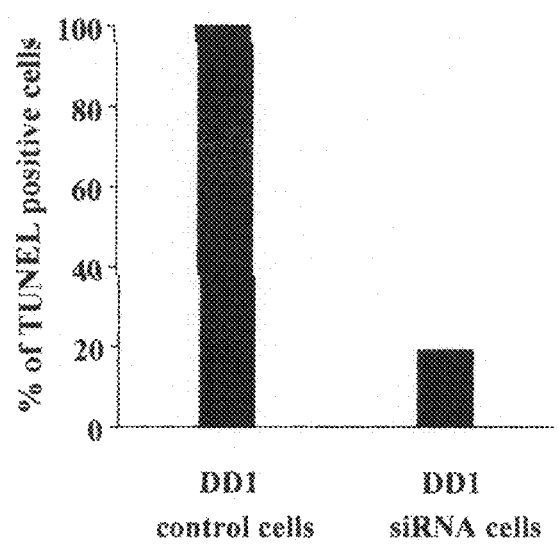

To explore this, we used an siRNA that had been previously shown to efficiently silence human caspase-2 expression in transfected cells (27). T-47D cells were first transfected with this caspase-2 siRNA. Forty-eight h later the cells were then harvested, re-plated, and transfected with GFPNLS-DD1 to monitor apoptosis induced by DD1. We found that DD1-mediated apoptosis was dramatically reduced in cells treated with the caspase-2 siRNA (FIGS. 6A and 6C). In contrast, mock-treated cells that did not receive caspase-2 siRNA underwent rapid apoptosis upon expression of DD1 (FIGS. 6A and 6C). Western analysis indicated that the level of caspase-2 protein was reduced by more than 5-fold in specific siRNA treated cells, demonstrating the effectiveness of the siRNA technique (data not shown). Consistent with the siRNA study, we found that zVDVAD-fmk, a chemical inhibitor of caspase-2, also efficiently blocked DD1-induced apoptosis in T-47D cells, suggesting a requirement for caspase-2 activity (data not shown). Interestingly, pre-treatment with the same caspase-2 siRNA had no effect on etoposide-induced apoptosis in T-47D cells (FIG. 6B), indicating that caspase-2 is not universally required for initiating apoptosis per se in these cells. The result of our etopside study is reminiscent of the finding by Lassus et al. showing that MCF-7 cells did not require caspase-2 for DNA damage-induced release of cytochrome-c (27). Thus, while caspase-2 is not essential for every intrinsic apoptotic program, our study here identifies a specific role for caspase-2 in DD1-mediated apoptosis in T-47D cells.

EXAMPLE 7

Figure 7A:
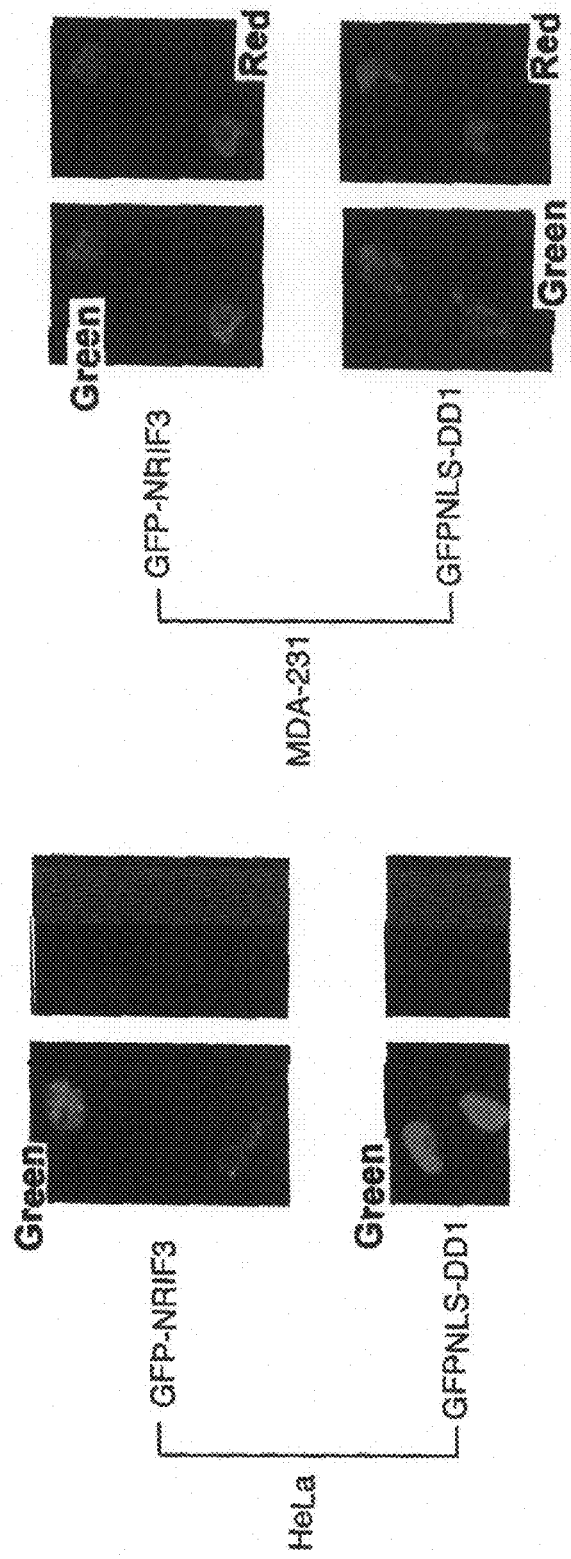
FIG. 7. (A and B) Cell-type specificity in cytotoxicity mediated by NRIF3 and DD1. (A) Various breast cancer cell lines and other cells were transfected with either GFP-NRIF3 or GFPNLS-DD1. Cells were examined for apoptosis by TUNEL assay (red). Representative fluorescent micrographs of transfected HeLa and MDA-MB-231 cells are compared. (B) A summary of results from all cell lines examined in (A). "+++" indicates profound apoptosis (>90% of green fluorescent cells were TUNEL positive) while "−" indicates no apoptosis (less than 2% positive).

Cell-type specificity in cytotoxicity mediated by NRIF3 and DD1. We previously reported that expression of NRIF3 enhances ligand-dependent transactivation by TR or RXR in HeLa cells (28). Thus, the finding of an apoptogenic function for NRIF3 in T-47D cells was unexpected. One possibility is that the apoptogenic effect of NRIF3 or DD1 is cell-type specific. In support of this notion, we found that expression of GFP-NRIF3 or GFPNLS-DD1 did not lead to apoptosis in HeLa cells (FIG. 7A).

The dramatic difference in cellular response to the expression of NRIF3 in T-47D cells (which exhibit 100% apoptosis) and HeLa cells (which show no apoptosis) suggests cell-type specificity in the cytotoxic effect mediated by NRIF3 and DD1. To further explore this, we examined 11 cell lines for the induction of apoptosis upon expression of NRIF3 or DD1. Five were breast cancer cell lines, including ER+T-47D and MCF-7 cells, ER− MB-MDA-231 and MB-MDA-435 cells, as well as an ER+derivative of MB-MDA-231 (2). We also examined HBL100 cells, a non-malignant but immortalized breast epithelial cell line (13). Remarkably, we found that expression of NRIF3 or DD1 resulted in efficient apoptosis in all 5 breast cancer cell lines, as well as in the immortalized HBL100 cells (FIGS. 7A and 7B, and data not shown).

In contrast, expression of NRIF3 or DD1 did not lead to apoptosis in any of the other 5 examined tumor cell lines (HeLa, 293, COS-1, UOK-145, GH4C1) which are not derived from breast epithelium (FIG. 7B). Thus, NRIF3 and DD1 appear to selectively induce apoptosis in breast cancer or related cells but not in the other cell types examined. This finding suggests that breast cancer cells contain a novel "death switch" that is specifically triggered by NRIF3 or DD1 (FIG. 8). We propose that triggering of this switch by NRIF3 (or DD1) results in activation of caspase-2, which in turn leads to further downstream events of apoptosis (FIG. 8).

EXAMPLE 8

Figure 9:
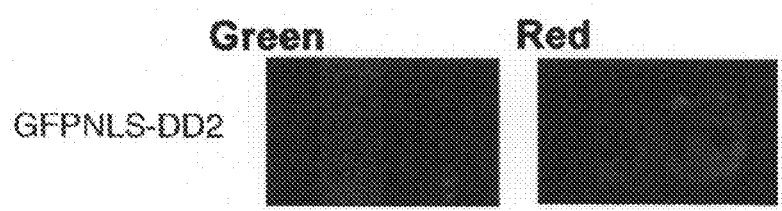
FIG. 9. NRIF3 contains a second death domain (DD2). Representative fluorescent micrographs are shown for T-47D cells transfected with a vector expressing GFPNLS-DD2 (DD2 corresponds to amino acid residues 47-86 of NRIF3). Cells were examined for apoptosis by TUNEL assay (red). In a control experiment, cells transfected with the GFPNLS control vector were not TUNEL positive (data not shown, but representative micrographs of cells transfected with GFP-NLS are shown in FIG. 3B).

NRIF3 contains two other death domains (DD2 and DD3). In addition to the death domain DD1 that is described in Example 3, we uncovered two additional death domains within the NRIF3 molecule. In one experiment, a region comprising amino acid residues 47 to 86 of NRIF3 (termed DD2) was fused in-frame with GFPNLS. The resulting vector expressing GFPNLS-DD2 was transfected into T-47D cells to examine the induction of apoptosis. As shown in FIG. 9, we found that green cells expressing GFPNLS-DD2 were TUNEL positive, indicating cell death. As a control, cells transfected with the GFPNLS control vector were not TUNEL positive (data not shown).

Figure 10:
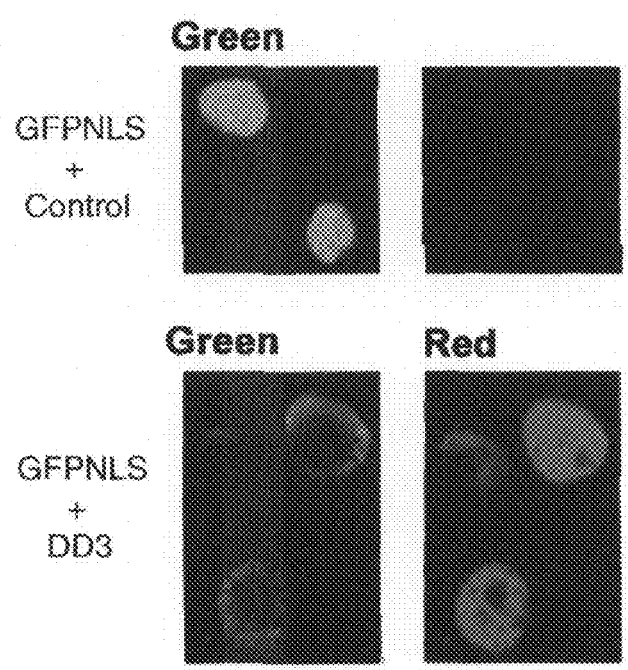
FIG. 10. NRIF3 contains a third death domain (DD3) (SEQ ID NO:13). T-47D cells were transfected to express GFP-NLS, along with either a control vector or a vector expressing DD3 (DD3 corresponds to amino acid residues 112 to 177 of NRIF3). About 24 h after transfection, the cells were fixed and subjected to TUNEL assay. The transfected cells were then visualized by fluorescent microscopy (green), and at the same time examined for apoptosis (red). Representative fluorescent micrographs of cells transfected with the control vector or DD3 are compared.

In another experiment, we transfected T-47D cells with vectors expressing a variety regions of NRIF3 fused in frame with the DNA binding domain of Gal4, and examined the transfected cells for induction of apoptosis. In each case, a vector expressing GFPNLS was cotransfected to visualize transfected cells (shown as green cells). Not surprisingly, we found that expression of Gal4-NRIF3, or Gal4-EnS, or Gal4-DD1 all induced rapid apoptosis in T-47D cells (data not shown), while expression of the Gal4 control did not result in cell death (FIG. 10). Interestingly, expression of a region comprising amino acid residues 112 to 177 of NRIF3 (termed DD3) as a Gal4-fusion resulted in efficient induction of apoptosis, as shown by the TUNEL assay (FIG. 10). Taken together, our results in FIG. 9 and FIG. 10 indicate that the NRIF3 molecule contains two additional death domains, a DD2 which resides from amino acid residues 47 to 86; and a DD3 which resides from amino acid residues 112 to 177.

Discussion

In this study we present a novel finding that expression of members of the NRIF3 family of co-regulators leads to rapid and profound apoptosis in a number of different breast cancer cell lines. Deletion analysis showed that apoptogenic effect of the NRIF3 family is mediated by a novel death domain (DD1) (residues 20-50, see FIG. 3). Interestingly, cytotoxicity of NRIF3 and DD1 appears to be specific to breast cancer or related cells, as their expression did not lead to apoptosis in other cell types such as HeLa cells (FIG. 7). Consistent with this, previous studies have shown that NRIF3 acts as a co-activator for TR and RXR in HeLa cells (28).

Apoptosis plays important roles in both normal tissue homeostasis and pathological processes such as tumorgenesis. Disruption of cellular apoptotic pathways often accompanies tumorgenesis and likely confers survival advantage to tumor cells (20). Since many anticancer drugs kill by inducing apoptosis, dysregulation of apoptosis could also lead to drug resistance (20). Although the progress in understanding mechanisms underlying apoptosis and its regulation/dysregulation in cancer cells presents opportunities to utilize the cellular death machinery for treating human diseases such as cancer (20, 35), how to deliver tumor-specific cytotoxicity without killing other innocent cells remains an important challenge.

Figure 4A:
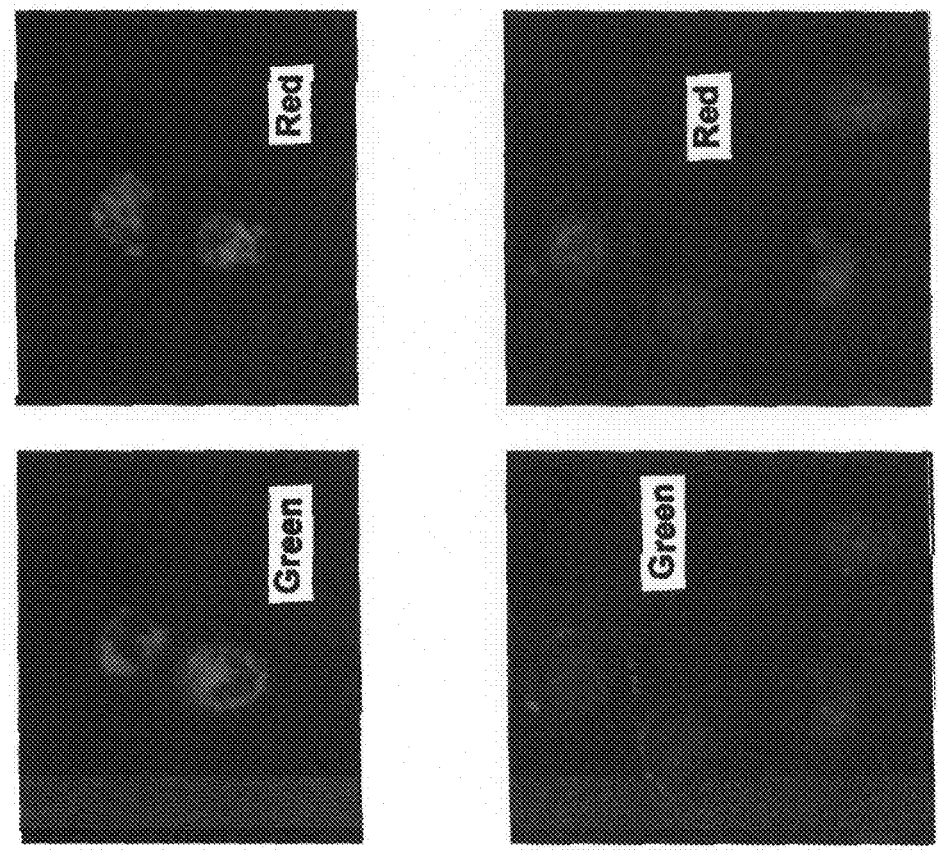
FIG. 4. (A and B) Cell death mediated by NRIF3 or DD1 is insensitive to zVAD-fmk. (A) T-47D cells were transfected with either GFP-NRIF3 or GFPNLS-DD1 in the absence or presence of the broad-spectrum caspase inhibitor zVAD-fmk. When present, the inhibitor was incubated with the cells before and after transfection. Cells were examined for apoptosis by TUNEL assay (red). Representative fluorescent micrographs are shown for cells treated with zVAD-fmk. (B) Quantitative presentation of the experiments in (A). The percent of green fluorescent cells that were TUNEL positive were scored for T-47D cells transfected with either GFP-NRIF3 or GFPNLS-DD1 in the absence or presence of zVAD-fmk.
Figure 4B:
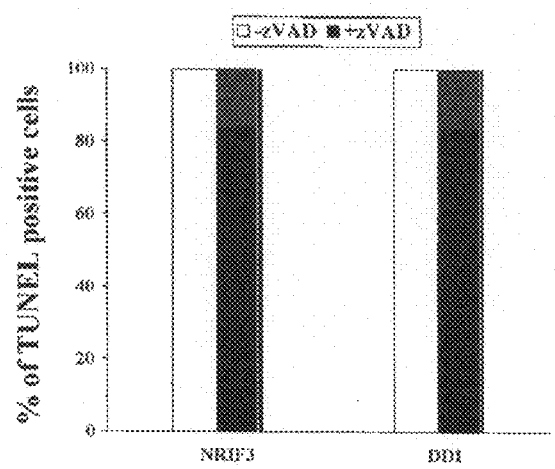

The data presented herein demonstrate that cytotoxicity can be selectively induced in a specific cancer, as NRIF3, DD1 and related molecules kill breast cancer but not other cells (FIG. 7). Since DD1 is devoid of regions involved in interaction with nuclear receptors (28, 29), it is unlikely that apoptosis mediated by NRIF3 or DD1 results from perturbation of nuclear receptor functions. DD1-induced apoptosis is inhibited by co-expression of Bcl-2 or Bcl-xL (FIGS. 5A and 5B, and data not shown), and is associated with the translocation of AIF from mitochondria to the nucleus (FIG. 5C), suggesting that cell death is mediated by a mitochondrial pathway (FIG. 8). Since AIF is capable of triggering apoptosis independent of effector caspases (8, 31, 46, 51), its rapid translocation from mitochondria to the nucleus is consistent with the finding that the broad-spectrum caspase inhibitor zVAD-fmk failed to block NRIF3- or DD1-induced cell death (FIGS. 4A and 4B).

The results of the siRNA study indicate that DD1-mediated apoptosis requires caspase-2 (FIG. 6). The same caspase-2 siRNA has no effect on etopside-induced apoptosis in T-47D cells (FIG. 6B), suggesting that its effect on DD1-mediated cell death is specific. The requirement for caspase-2 is not inconsistent with the zVAD-fmk results, as caspase-2 is much more resistant to zVAD-fmk than other caspases (14). Interestingly, several recent studies have identified a novel apical initiator role for caspase-2 during stress-induced apoptosis, where it acts upstream of mitochondria and is required for MMP (17, 27, 42). Without wishing to be bound by theory, it is believed that expression of NRIF3 or DD1 in breast cancer cells triggers activation of caspase-2, which then promotes MMP, leading to the release of AIF and subsequent downstream events of apoptosis (see FIG. 8). Interestingly, expression of caspase-2-GFP in T-47D cells resulted in nuclear localization of the GFP signal (Dr. Honglin Li, personal communication). This finding is consistent with the model above, as members of the NRIF3 family and DD1 trigger apoptosis in breast cancer cells while being primarily (if not exclusively) localized to the nucleus (FIGS. 1B, 2B, and 3B).

Although caspase-2 functions upstream of mitochondria in certain intrinsic apoptotic pathways, the molecular mechanism(s) underlying activation of caspase-2 (upon apoptotic stimuli) is not yet understood (24, 48). Activation of other initiator caspases such as caspase-8 and -9 is thought be to be mediated by a dimerization mechanism that does not require proteolytic cleavage (6). It is conceivable that caspase-2 could be activated similarly by complex formation and/or dimerization (9, 40, 48). In this respect, NRIF3 or DD1 may function in breast cancer cells by regulating and/or participating in the process of caspase-2 activation. Interestingly, Western blot analysis showed that caspase-2 is expressed at similar levels in T-47D, MDA-MB-231, HeLa, and 293 cells (unpublished observations), despite the fact that NRIF3 or DD1 only induces cytotoxicity in T-47D and MDA-MB-231, but not in HeLa and 293 cells (FIG. 7). Thus, a simple mechanism such as direct activation of caspase-2 by NRIF3 or DD1 via a bilateral protein-protein interaction seems unlikely.

The detailed mechanism(s) notwithstanding, these results indicate that cytotoxicity of NRIF3, DD1 and related molecules is cell-type specific. It is possible that NRIF3 or DD1 could act by specifically tipping the balance between pro- and anti-apoptotic factors for breast cancer cells, e.g., by blocking the effect of a specific anti-apoptotic factor(s) or by enhancing the effect of a specific pro-apoptotic factor(s). However, a survey of a number of such factors (including Bcl-2, Bcl-xL, Bax, Bak, caspase-3, and p53) in a variety of breast cancer cells did not identify any unique pattern of expression among these cells (53). Thus, the apoptogenic function of NRIF3 or DD1 may be mediated by a yet-to-be defined breast cancer cell-specific "death switch". Triggering of this "switch" by NRIF3 or DD1 results in activation of caspase-2 which in turn leads to further downstream events of apoptosis such as MMP (see FIG. 8 for the model). Despite an extensive literature on apoptosis in breast cancer cells, very few if any previous studies have explored the role of caspase-2.

The finding that the S28A mutation significantly reduced the ability of mutant DD1 to induce apoptosis in T-47D cells (FIGS. 3B and 3C) suggests that apoptogenic activity of DD1 (or NRIF3) can be regulated by phosphorylation. However, the S28A mutant can still manifest some apoptogenic activity (about 20% cell death, see FIG. 3C), indicating that phosphorylation of Ser28 is not absolutely required for induction of apoptosis. In contrast, expression of DD1 resulted in no detectable cell death in non-responsive cells such as HeLa and 293 (FIG. 7). In addition, it was previously shown that phosphorylation of Ser28 is essential for the transrepression function harbored by the same DD1 region (29). Interestingly, wild type DD1 mediates significant repression in cells such as HeLa and GH4C1 while the repression is abolished by the S28A mutation (29). These results suggest that Ser28 is phosphorylated in HeLa or GH4C1 cells despite the finding that they do not undergo apoptosis in response to DD1 expression. Thus, differential phosphorylation of DD1 (or lack of) in different cell types are unlikely to be the main mechanism accounting for the breast cancer cell-specific death switch proposed in FIG. 8.

Figure 3C:
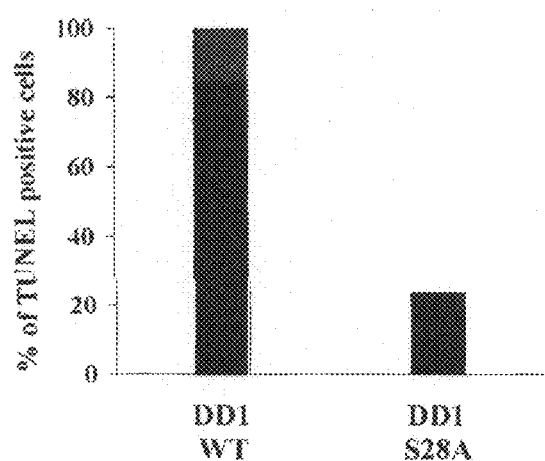

The above results here bear a number of potential therapeutic implications. Strategies utilizing the breast cancer-specific cytotoxicity of NRIF3, DD1 and related molecules allows for the development of novel antitumor agents against breast cancer. The relative compact size of DD1 (only ~30 amino acids) is an attractive feature in this respect. It is also interesting to note that phosphorylation of Ser28 appears to be important for the apoptogenic function of DD1 (FIGS. 3B and 3C). Identification of the candidate kinase that phosphorylates DD1 and understanding the underlying regulatory mechanism may provide an opportunity to enhance apoptogenic function of NRIF3 or DD1 for therapeutic purposes. Low levels of NRIF3 mRNA can be detected in T-47D and MCF-7 cells by RT-PCR (unpublished observations). Future study of mechanism(s) regulating expression of the NRIF3 family in breast cancer cells may lead to novel means to promote apoptosis in these cells by up-regulating their expression. Finally, our study raises an intriguing possibility that cell-specific mechanism(s) might be employed in activation of caspase-2, and thus, similar but not identical "death switches" may exist in other cancer cells as well. Targeting these switches would represent novel strategies in developing new and more selective therapeutics against cancer.

REFERENCES

1. Adam, S. A., and L. Gerace. 1991. Cytosolic proteins that specifically bind nuclear location signals are receptors for nuclear import. Cell 66:837-847.
2. Afonja, A., B. M. Raaka, A. Huang, S. Das, X. Zhao, E. Helmer, D. Juste, and H. H. Samuels. 2002. RAR Agonists Stimulate SOX9 Gene Expression in Breast Cancer Cell Lines: Evidence for a Role in Retinoid-Mediated Growth Inhibition. Oncogene 21:7850-7860.
3. Antonsson, B. 2001. Bax and other pro-apoptotic Bcl-2 family "killer-proteins" and their victim the mitochondrion. Cell Tissue Res. 306:347-361.
4. Baliga, B. C., P. A. Colussi, S. H. Read, M. M. Dias, D. A. Jans, and S. Kumar. 2003. Role of prodomain in importin-mediated nuclear localization and activation of caspase-2. J. Biol. Chem. 278:4899-4905.
5. Benson, J. R., and V. Pitsinis. 2003. Update on clinical role of tamoxifen. Curr. Opin. Obstet. Gynecol. 15:13-23.
6. Boatright, K. M., M. Renatus, F. L. Scott, S. Sperandio, H. Shin, I. M. Pedersen, J. E. Ricci, W. A. Edris, D. P. Sutherlin, D. R. Green, and G. S. Salvesen. 2003. A unified model for apical caspase activation. Mol. Cell. 11:529-541.
7. Borner, C. 2003. The Bcl-2 protein family: sensors and checkpoints for life- or -death decisions. Mol. Immunol. 39:615-647.
8. Cande, C., I. Cohen, E. Daugas, L. Ravagnan, N. Larochette, N. Zamzami, and G. Kroemer. 2002. Apoptosis-inducing factor (AIF): a novel caspase-independent death effector released from mitochondria. Biochimie 84:215-222.
9. Chang, D. W., D. Ditsworth, H. Liu, S. M. Srinivasula, E. S. Alnemri, and X. Yang. 2003. Oligomerization is a general mechanism for the activation of apoptosis initiator and inflammatory procaspases. J. Biol. Chem. 278:16466-16469.
10. Chen, G., and D. V. Goeddel. 2002. TNF-R1 signaling: a beautiful pathway. Science 296:1634-1635.
11. Cohen, G. M. 1997. Caspases: the executioners of apoptosis. Biochem. J. 326:1-16.
12. Colussi, P. A., N. L. Harvey, and S. Kumar. 1998. Pro-domain-dependent nuclear localization of the caspase-2 (Nedd2) precursor. A novel function for a caspase pro-domain. J. Biol. Chem. 273:24535-24542.
13. Dimri, G. P., J. L. Martinez, J. J. Jacobs, P. Keblusek, K. Itahana, M. Van Lohuizen, J. Campisi, D. E. Wazer, and V. Band. 2002. The Bmi-1 oncogene induces telomerase activity and immortalizes human mammary epithelial cells. Cancer Res. 62:4736-4745.
14. Ekert, P. G., J. Silke, and D. L. Vaux. 1999. Caspase inhibitors. Cell Death Differ. 6:1081-1086.
15. Fitzgerald, P., M. Teng, R. A. Chandraratna, R. A. Heyman, and E. A. Allegretto. 1997. Retinoic acid receptor alpha expression correlates with retinoid-induced growth inhibition of human breast cancer cells regardless of estrogen receptor status. Cancer Res. 57:2642-2650.
16. Gavrieli, Y., Y. Sherman, and S. A. Ben-Sasson. 1992. Identification of programmed cell death in situ via specific labeling of nuclear DNA fragmentation. J. Cell Biol. 119:493-501.
17. Guo, Y., S. M. Srinivasula, A. Druilhe, T. Fernandes-Alnemri, and E. S. Alnemri. 2002. Caspase-2 induces apoptosis by releasing proapoptotic proteins from mitochondria. J. Biol. Chem. 277:13430-13437.
18. Hengartner, M. 0.2000. The biochemistry of apoptosis. Nature 407:770-776.
19. Homburg, C. H., M. de Haas, A. E. von dem Borne, A. J. Verhoeven, C. P. Reutelingsperger, and D. Roos. 1995. Human neutrophils lose their surface Fc gamma RIII and acquire Annexin V binding sites during apoptosis in vitro. Blood 85:532-540.
20. Johnstone, R. W., A. A. Ruefli, and S. W. Lowe. 2002. Apoptosis: a link between cancer genetics and chemotherapy. Cell 108:153-164.
21. Kastner, P., M. Mark, and P. Chambon. 1995. Nonsteroid nuclear receptors: what are genetic studies telling us about their role in real life? Cell 83:859-869.
22. Kastner, P., M. Mark, N. Ghyselinck, W. Krezel, V. Dupe, J. M. Grondona, and P. Chambon. 1997. Genetic evidence that the retinoid signal is transduced by heterodimeric RXR/RAR functional units during mouse development. Development 124:313-326.
23. Kumar, R., R. K. Vadlamudi, and L. Adam. 2000. Apoptosis in mammary gland and cancer. Endocr. Relat. Cancer 7:257-269.
24. Kumar, S., and D. L. Vaux. 2002. Apoptosis. A cinderella caspase takes center stage. Science 297:1290-1291.
25. Kuwana, T., M. R. Mackey, G. Perkins, M. H. Ellisman, M. Latterich, R. Schneiter, D. R. Green, and D. D. Newmeyer. 2002. Bid, Bax, and lipids cooperate to form supramolecular openings in the outer mitochondrial membrane. Cell 111:331-342.

26. Lahm, A., A. Paradisi, D. R. Green, and G. Melino. 2003. Death fold domain interaction in apoptosis. Cell Death Differ. 10:10-12.
27. Lassus, P., X. Opitz-Araya, and Y. Lazebnik. 2002. Requirement for caspase-2 in stress-induced apoptosis before mitochondrial permeabilization. Science 297:1352-1354.
28. Li, D., V. Desai-Yajnik, E. Lo, M. Schapira, R. Abagyan, and H. H. Samuels. 1999. NRIF3 is a novel coactivator mediating functional specificity of nuclear hormone receptors. Mol. Cell. Biol. 19:7191-7202.
29. Li, D., F. Wang, and H. H. Samuels. 2001. Domain Structure of the NRIF3 Family of Coregulators Suggests Potential Dual Roles in Transcriptional Regulation. Mol. Cell. Biol. 21:8371-8384.
30. Li, H., H. Zhu, C. J. Xu, and J. Yuan. 1998. Cleavage of BID by caspase 8 mediates the mitochondrial damage in the Fas pathway of apoptosis. Cell 94:491-501.
31. Loeffler, M., E. Daugas, S. A. Susin, N. Zamzami, D. Metivier, A. L. Nieminen, G. Brothers, J. M. Penninger, and G. Kroemer. 2001. Dominant cell death induction by extramitochondrially targeted apoptosis-inducing factor. Faseb J. 15:758-767.
32. Madesh, M., B. Antonsson, S. M. Srinivasula, E. S. Alnemri, and G. Hajnoczky. 2002. Rapid kinetics of tBid-induced cytochrome c and Smac/DIABLO release and mitochondrial depolarization. J. Biol. Chem. 277:5651-5659.
33. Mangelsdorf, D. J., C. Thummel, M. Beato, P. Herrlich, G. Schutz, K. Umesono, B. Blumberg, P. Kastner, M. Mark, P. Chambon, and R. M. Evans. 1995. The nuclear receptor superfamily: the second decade. Cell 83:835-839.
34. Miura, M., R. M. Friedlander, and J. Yuan. 1995. Tumor necrosis factor-induced apoptosis is mediated by a CrmA-sensitive cell death pathway. Proc. Natl. Acad. Sci. USA 92:8318-8322.
35. Nicholson, D. W. 2000. From bench to clinic with apoptosis-based therapeutic agents. Nature 407:810-816.
36. Ohtoshi, A., and H. Otoshi. 2001. Analysis of beta3-endonexin mutants for their ability to interact with cyclin A. Mol. Genet. Genomics 266:664-671.
37. Paroni, G., C. Henderson, C. Schneider, and C. Brancolini. 2002. Caspase-2 can trigger cytochrome C release and apoptosis from the nucleus. J. Biol. Chem. 277:15147-15161.
38. Penninger, J. M., and G. Kroemer. 2003. Mitochondria, AIF and caspases—rivaling for cell death execution. Nat. Cell Biol. 5:97-99.
39. Raffo, P., L. Emionite, L. Colucci, F. Belmondo, M. G. Moro, W. Bollag, and S. Toma. 2000. Retinoid receptors: pathways of proliferation inhibition and apoptosis induction in breast cancer cell lines. Anticancer Res. 20:1535-1543.
40. Read, S. H., B. C. Baliga, P. G. Ekert, D. L. Vaux, and S. Kumar. 2002. A novel Apaf-1-independent putative caspase-2 activation complex. J. Cell Biol. 159:739-745.
41. Riggs, B. L., and L. C. Hartmann. 2003. Selective estrogen-receptor modulators—mechanisms of action and application to clinical practice. N. Engl. J. Med. 348:618-629.
42. Robertson, J. D., M. Enoksson, M. Suomela, B. Zhivotovsky, and S. Orrenius. 2002. Caspase-2 acts upstream of mitochondria to promote cytochrome c release during etoposide-induced apoptosis. J. Biol. Chem. 277:29803-29809.
43. Schneider, S. M., M. Offterdinger, H. Huber, and T. W. Grunt. 2000. Activation of retinoic acid receptor alpha is sufficient for full induction of retinoid responses in SK-BR-3 and T47D human breast cancer cells. Cancer Res. 60:5479-5487.
44. Shattil, S. J., T. O'Toole, M. Eigenthaler, V. Thon, M. Williams, B. M. Babior, and M. H. Ginsberg. 1995. b3-endonexin, a novel polypeptide that interacts specifically with the cytoplasmic tail of the integrin b3 subunit. J. Cell Biol. 131:807-816.
45. Shikama, Y., M. U, T. Miyashita, and M. Yamada. 2001. Comprehensive studies on subcellular localizations and cell death-inducing activities of eight GFP-tagged apoptosis-related caspases. Exp. Cell Res. 264:315-325.
46. Susin, S. A., H. K. Lorenzo, N. Zamzami, I. Marzo, B. E. Snow, G. M. Brothers, J. Mangion, E. Jacotot, P. Costantini, M. Loeffler, N. Larochette, D. R. Goodlett, R. Aebersold, D. P. Siderovski, J. M. Penninger, and G. Kroemer. 1999. Molecular characterization of mitochondrial apoptosis-inducing factor. Nature 397:441-446.
47. Talanian, R. V., C. Quinlan, S. Trautz, M. C. Hackett, J. A. Mankovich, D. Banach, T. Ghayur, K. D. Brady, and W. W. Wong. 1997. Substrate specificities of caspase family proteases. J. Biol. Chem. 272:9677-9682.
48. Troy, C. M., and M. L. Shelanski. 2003. Caspase-2 redux. Cell Death Differ. 10:101-107.
49. Verhoven, B., R. A. Schlegel, and P. Williamson. 1995. Mechanisms of phosphatidylserine exposure, a phagocyte recognition signal, on apoptotic T lymphocytes. J. Exp. Med. 182:1597-1601.
50. Wang, X. 2001. The expanding role of mitochondria in apoptosis. Genes Dev. 15:2922-2933.
51. Ye, H., C. Cande, N. C. Stephanou, S. Jiang, S. Gurbuxani, N. Larochette, E. Daugas, C. Gamido, G. Kroemer, and H. Wu. 2002. DNA binding is required for the apoptogenic action of apoptosis inducing factor. Nat. Struct. Biol. 9:680-684.
52. Yoshida, H. 2003. The role of apaf-1 in programmed cell death: from worm to tumor. Cell Struct. Funct. 28:3-9.
53. Zapata, J. M., M. Krajewska, S. Krajewski, R. P. Huang, S. Takayama, H. G. Wang, E. Adamson, and J. C. Reed. 1998. Expression of multiple apoptosis-regulatory genes in human breast cancer cell lines and primary tumors. Breast Cancer Res. Treat. 47:129-1240.
54. Adjuvant Therapy for Breast Cancer NIH Consensus Statement 2000, November 1-3; 17[4]: 1-35

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description purposes.

Patents, patent applications, publications, product descriptions, and protocols are cited throughout this application, the disclosures of which are incorporated herein by reference in their entireties for all purposes.

What is claimed is:

1. A pharmaceutical composition for killing breast cancer cells comprising (i) an expression construct encoding a polypeptide consisting of the sequence DD1 (SEQ ID NO: 11), which is optionally linked to a heterologous sequence, wherein said construct is present in an amount effective for killing breast cancer cells, and (ii) a pharmaceutically acceptable carrier or diluent.

2. The pharmaceutical composition of claim 1, wherein the expression construct further comprises a viral vector.

3. The pharmaceutical composition of claim 1, wherein the expression construct further comprises a naked DNA plasmid sequence.

4. The pharmaceutical composition of claim 1, wherein the expression construct comprises the nucleotide sequence DD1 (SEQ ID NO: 4).

5. The pharmaceutical composition of claim 1, wherein the composition causes apoptosis in a breast cancer cell.

* * * * *